US007727526B2

(12) United States Patent
Massfelder et al.

(10) Patent No.: US 7,727,526 B2
(45) Date of Patent: Jun. 1, 2010

(54) USE OF PTHRP ANTAGONISTS FOR TREATING RENAL CELL CARCINOMA

(75) Inventors: Thierry Massfelder, Witternheim (FR); Herve Lang, Strasbourg (FR); Eric Schordan, Handschuheim (FR); Jean-Jacques Helwig, Schiltigheim (FR)

(73) Assignees: Universite Louis Pasteur, Strasbourg (FR); Institut National de la Sante et de la Recherche Medicale (INSERM), Paris Cedex (FR); Hopitaux Universitaires de Strasbourg, Strasbourg Cedex (FR)

( * ) Notice: Subject to any disclaimer, the term of this patent is extended or adjusted under 35 U.S.C. 154(b) by 59 days.

(21) Appl. No.: 10/520,085

(22) PCT Filed: Jul. 4, 2003

(86) PCT No.: PCT/FR03/02084

§ 371 (c)(1),
(2), (4) Date: Apr. 18, 2005

(87) PCT Pub. No.: WO2004/004756

PCT Pub. Date: Jan. 15, 2004

(65) Prior Publication Data

US 2006/0003916 A1    Jan. 5, 2006

(30) Foreign Application Priority Data

Jul. 5, 2002    (FR) .................................. 02 08501

(51) Int. Cl.
*A61K 39/395*    (2006.01)
*A61K 39/00*    (2006.01)

(52) U.S. Cl. ................................. 424/139.1; 424/130.1

(58) Field of Classification Search ........................ None
See application file for complete search history.

(56) References Cited

U.S. PATENT DOCUMENTS 6,903,194 B1    6/2005 Sato et al.

FOREIGN PATENT DOCUMENTS

| EP | 1 197 225 A1 | 4/2002 |
|----|----|----|
| EP | 1197225 A1 * | 4/2002 |
| EP | 1 283 057 A1 | 2/2003 |
| WO | WO 96/22790 | 8/1996 |
| WO | WO 97/04312 | 2/1997 |
| WO | WO 01/85784 | 11/2001 |

OTHER PUBLICATIONS

Hoare, S.R.J. and Usdin, T.B. Specificity and stability of a new PTH1 receptor antagonist, mouse TIP(7-39). Peptides, 2002. vol. 23, pp. 989-998.*

Bachmann, M.F., Wolint, P., Schwarz, K., and Oxenius, A. Recall proliferation potential of memory CD8+ T cells and antiviral protection. 2005, Journal of Immunology, vol. 175, pp. 4677-4685.*
Burton, P.B.J., Moniz, C., and Knight, D. Parathyroid hormone related peptide can function as an autocrine growth factor in human renal cell carcinoma. 1990, Biochemical and biophysical research communications, vol. 167, No. 3, pp. 1134-1138.*
Efferson, C.L., Kawano, K., Tsuda, N., Palese, P., Garcia-Sastre, A., and Ioannides, C.G. Stimulation of human T cells by an influenza A vector expressing a CTL epitope from the HER-2/neu protooncogene results in higher numbers of antigen-specific TCRhi cells than stimulation with peptide. 2005, Anticancer Research, vol. 25, pp. 715-724.*
Wheeler, C.M. Preventive vaccines for cervical cancer. 1997. Salud Publica de Mexico, vol. 39, No. 4, pp. 1-9.*
Drucker, B.J. Renal Cell Carcinoma: Current status and future prospects, 2005. Cancer Treatment Reviews, vol. 31, pp. 536-545.*
Iwamura, M., Wu, W., Muramoto, M., Ohori, M., Egawa, S., Uchida, T., and Baba, S. Parathyroid hormone-related protein is an independent prognostic factor for renal cell carcinoma. Cancer, 1999. vol. 86 No. 6, pp. 1028-1034.*
Massfelder, Lang, Schordan, Kinder, Rothhut, Welsch, Simon-Assmann, Barthelmebs, Jacqmin, and Helwig. Parathyroid hormone-related protein is an essential growth factor for human clear cell renal carcinoma and a target for the von Hippel-Lindau tumor suppressor gene. Cancer Research, 2004. vol. 64, pp. 180-188.*
Burton et al, Biochemical and Biophysical Research Communications, 1990, vol. 167, No. 3, pp. 1134-1138.
Savage et al, Journal of Endocrinology, 1993, vol. 137, No. suppl., p. P57.
Hoare et al, Peptides, 2002, vol. 23, No. 5, pp. 989-998.
Akino et al, Endocrinology, 2000, vol. 141, No. 11, pp. 4313-4316.
Luparello et al, "Midregion Parathyroid Hormone-Related Protein Inhibits Growth and Invasion In Vitro and Tumorigenesis In Vivo of Human Breast Cancer Cells", Journal of Bone and Mineral Research, 2001, vol. 16, No. 12, pp. 2173-2181.
Esaki et al "The selection of therapeutic antibodies by kenetic analysis" Biocore Journal—No. 2 2002, pp. 7-8)) obtained from a hybridoma (such as the hybridoma #23-57-137-1.
Okada et al "Immunohistochemical Localization of Parathyroid Hormone-related Protein in Canine Mammary Tumors" Vet Pathol 34: 356-359 (1997).
Verheijen et al, "Parathyroid hormone-related peptide (PTHrP) induces parietal endoderm formation exclusively via the Type I PTH/PTHrP receptor" Mechanisms of Development 81 (1999) 151-161.
Thorikay et al., "Synthesis of a gene encoding parathyroid hormone-like protein-(1-141): purification and biological characterization of the expressed protein" Endocrinology, vol. 124, 111-118 (1989).

(Continued)

*Primary Examiner*—Larry R. Helms
*Assistant Examiner*—Anne M. Gussow
(74) *Attorney, Agent, or Firm*—Nixon & Vanderhye P.C.

(57) ABSTRACT

The present invention concerns the use of a PTHrP antagonist for preparing a pharmaceutical composition for treating renal cell carcinoma (RCC) in a mammal and in particular in a human subject. Advantageously, the invention is of particular interest for inhibiting or reducing tumour growth and/or metastasis formation in kidney cancer and its metastatic developments, in particular in the lung and the liver.

12 Claims, 19 Drawing Sheets

OTHER PUBLICATIONS

Figure 1:
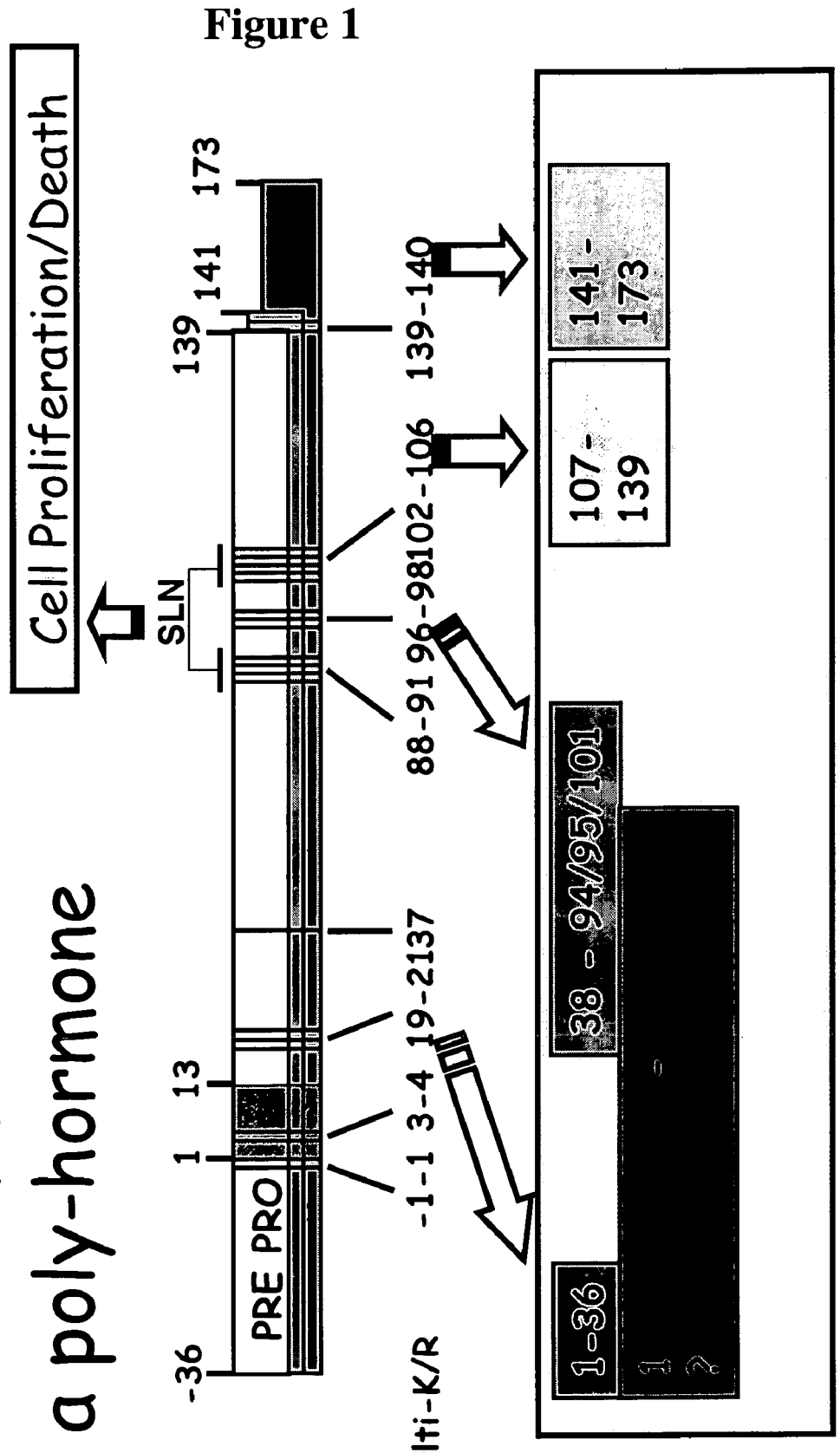

Fenton et al., "A carboxyl-terminal peptide from the parathyroid hormone-related protein inhibits bone resorption by osteoclasts." Endocrinology. Oct. 1991;129(4):1762-8 (Abstract).

Santos et al "Up-regulation of parathyroid hormone-related protein in folic acid-induced acute renal failure" Kidney International, vol. 60 (2001), pp. 982-995.

Garcia-Ocana et al "Cyclosporine increases renal parathyroid hormone-related protein expression in vivo in the rat" transplantation, vol. 65, 860-863, No. 6, Mar. 27, 1998.

Richard, et al. "Humoral Hypercalcemia of Malignancy, Severe Combined Immunodeficient/Beige Mouse Model of Adult T-Cell Lymphoma Independent of Human T-Cell Lymphotropic Virus Type-1 Tax Expression" Am J Pathol. Jun. 2001; 158(6): 2219-2228.

* cited by examiner

Treatment by antagonist

Control Treatment

SEQUENCE LISTING

```
<160> NUMBER OF SEQ ID NOS: 8

<210> SEQ ID NO 1
<211> LENGTH: 21
<212> TYPE: DNA
<213> ORGANISM: artificial sequence
<220> FEATURE:
<223> OTHER INFORMATION: primer

<400> SEQUENCE: 1
atgcgacgga gactggttca g                                                 21

<210> SEQ ID NO 2
<211> LENGTH: 33
<212> TYPE: DNA
<213> ORGANISM: artificial sequence
<220> FEATURE:
<223> OTHER INFORMATION: primer

<400> SEQUENCE: 2
tcaatgcctc cgtgaatcga gctccagcga cgt                                    33

<210> SEQ ID NO 3
<211> LENGTH: 22
<212> TYPE: DNA
<213> ORGANISM: artificial sequence
<220> FEATURE:
<223> OTHER INFORMATION: primer

<400> SEQUENCE: 3
aggaacagat cttcctgctg ca                                                22

<210> SEQ ID NO 4
<211> LENGTH: 24
<212> TYPE: DNA
<213> ORGANISM: artificial sequence
<220> FEATURE:
<223> OTHER INFORMATION: primer

<400> SEQUENCE: 4
```

```
cacagctacg gtgagggacg ccag                                              24

<210> SEQ ID NO 5
<211> LENGTH: 19
<212> TYPE: DNA
<213> ORGANISM: artificial sequence
<220> FEATURE:
<223> OTHER INFORMATION: primer

<400> SEQUENCE: 5
gcgtcgtgct gcccgtatg                                                    19

<210> SEQ ID NO 6
<211> LENGTH: 23
<212> TYPE: DNA
<213> ORGANISM: artificial sequence
<220> FEATURE:
<223> OTHER INFORMATION: primer

<400> SEQUENCE: 6
ttctgcacat ttgggtggtc ttc                                               23

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
ggaaggtgaa ggtcggagtc                                                   20

<210> SEQ ID NO 8
<211> LENGTH: 19
<212> TYPE: DNA
<213> ORGANISM: artificial sequence
<220> FEATURE:
<223> OTHER INFORMATION: primer

<400> SEQUENCE: 8
gcagtgatgg catggactg                                                    19
```

USE OF PTHRP ANTAGONISTS FOR TREATING RENAL CELL CARCINOMA

This application is the US national phase of international application PCT/FR2003/002084 filed 4 Jul. 2003, which designated the U.S. and claims benefit of FR 02/08501, dated 5 Jul. 2002, the entire contents of each of which are hereby incorporated by reference.

The object of the present invention is the use of at least one PTHrP antagonist for preparing a pharmaceutical composition for treating renal cell carcinoma (RCC) in a mammal and in particular in a human subject. Advantageously, the invention is of particular interest for inhibiting or reducing tumour growth and/or metastasis formation in kidney cancer and its metastatic developments, in particular in the lung and the liver.

The parathyroid hormone-related protein (or PTHrP) is a poly-hormone. It was discovered in 1987 on the basis of hypercalcaemic tumours in the human subject and is recognised today as being the main factor responsible for malignant humoral hypercalcaemia syndrome, a para-neoplasic syndrome associated with a large number of tumours (Philbrick W. M. et al., *Physiol. Rev,* 76:127-73, 1996).

Besides tumours, PTHrP is ubiquitously expressed by normal tissues where it appears in particular as a new factor which locally regulates growth, differentiation and death of cells. Its biological importance is clearly shown by premature death in utero of mice, in which the PTHrP gene or that of its receptor (the common receptor PTH/PTHrP or RPTH1) have been knocked out. The kidney does not escape this rule: PTHrP is expressed in all the functional components of the kidney (vessels, glomerules, tubules) and has effects there on the proliferation and differentiation of cells under normal and pathological conditions. The inventors of the present invention have considerably contributed in demonstrating these properties.

Three PTHrP isoforms have been identified. In the human subject the PTHrP gene (chromosome 12) codes for 3 isoforms of 139, 141 and/or 173 amino acids (only the forms of 139 and/or 141 amino acids are present in lower species: mice, rats, rabbits, etc.). These isoforms contain in their primary structure a certain number of multi-basic sites (multi-K/R) which serve as post-translational sites of proteolysis allowing the generation of several fragments which are all biologically active: an amino-terminal fragment (1-36) which contains a partial sequence homology with the parathyroid hormone (8 amino acids of the first 13 are identical between the parathyroid hormone, named PTH, and PTHrP); an intermediate form (38-94/95/101) and carboxy-terminal forms (107-139) and probably, in the human subject only, one form (141-173) (Philbrick et al., *Physiol Rev.* 76: 127-173, 1996; Wu et al., *J. Biol. Chem.,* 271: 24371-24381, 1996). Besides, combinations of the various forms listed below can also be secretion fragments. Thus, for example, during malignant humoral hypercalcaemia, one of the fragments secreted by the tumours is an amino-terminal fragment further containing the intermediate region, the carboxy-terminal end of which is still unknown (fragment represented by par (1-?) in FIG. 1).

The biological roles of PTHrP can be summarised as follows:
myorelaxation of the smooth vascular and extra-vascular muscles (amino-terminal fragments),
the regulation of trans-epithelial transport of calcium in the kidney, the placenta and the mammary gland (intermediate fragments),
major role during development which has been shown by early lethality in utero of knockout mice for the PTHrP gene or its receptor (Philbrick et al., *Physiol. Rev,* 76: 127-173,1996),
regulation of cell proliferation and differentiation and also cell death (all the fragments).

It is interesting to mention that the multi-basic sequences present in the intermediate region of the molecule serve in reality not only as post-translational sites of proteolysis but also as nuclear localisation sites allowing the molecule to be directed towards the nucleus of the cell and from there to regulate proliferation, cell differentiation and cell death by mechanisms which are yet unknown.

At the present time, only the receptor binding the amino-terminal fragments has been cloned, the common receptor PTH/PTHrP, named RPTH1. Pharmacological data exist regarding the existence of specific receptors of intermediate and carboxy-terminal forms.

Furthermore, it has recently been shown that PTHrP not only presents angiogenic activities on the endothelial cells in culture but also that it is capable of stimulating the expression of the endothelial factor derived from the endothelium (vascular endothelial-derived growth factor—VEGF) in various cell lines (Akino et al., *Endocrinology,* 141: 4313-4316, 2000 ; Esbrit et al., *J. Am. Soc. Nephrol.,* 11:1085-1092, 2000).

Renal cell carcinoma (RCC) is the most frequent group of tumours of the kidney as it represents approximately 80 to 85% of all tumours of the kidney in adults. RCC can be broken down into 5 sub-types from a pathological viewpoint, clear cell carcinoma (CCC, including the variant with acidophile cells) being the majority form since it represents approximately 85% of RCC. The other sub-types in decreasing order of incidence are papillary carcinoma (chromophiles), chromophobe cell carcinoma, Bellini carcinoma and unclassified renal cell carcinomas. Clear cell carcinoma (CCC) of the kidney which represents approximately 75% of malignant tumours of the kidney and 2% of deaths connected with cancer in France and throughout the world (7000 cases/year and 3500 deaths in France in 2000; 200,000 cases/year and 100,000 deaths/year throughout the world) is a hypervascularised tumour which originates in the proximal tubular epithelium of the kidney. The properties of PTHrP described below with on the one hand the description of a regulator effect of PTHrP upon the proliferation of renal proximal tubular cells (Garcia-Ocana et al, *J. Bone Miner. Res.,* 10 : 1875-1884, 1995 et Garcia-Ocana et al, *J. Am. Soc. Nephrol.,* 10: 238-244, 1999) and on the other hand the observations that immuno-reactive PTHrP is found in tumours in 95% of patients affected by CCC (Iwamura et al, Cancer, 86: 1028-1034, 1999), whatever their calcium level, have caused the authors of the present invention to research the role of the PTHrP/RPTH1 system in the development, growth and neo-vascularisation of these tumours. This is with the hope of being able to develop an efficient therapeutic approach to RCC and in particular CCC, particularly in its metastatic form, based upon the use of the components of the PTHrP/RPTH1 system.

In fact, with the exception of total or partial nephrectomy applicable to localised tumours, no therapy is at the present time effective against the metastatic forms of these tumours, with the latter being very resistant to the traditional treatments, whether it be hormone therapy, chemotherapy, radiotherapy and to a lesser degree (rate of response lower than 15%) immunotherapy (based on interleukins and interferons). Thus, currently no therapy is really effective against kidney cancer while its incidence is constantly rising (45% between 1980 and 2000) and the survival rate is 5% for 5 years in the case of metastatic effects.

One of the important aspects is that one of the factors favouring renal cell carcinoma is the Von Hippel-Lindau disease (VHL) (Motzer et al., *New Engl. J. Med.,* 335: 865-875, 1996). In fact, this disease is characterised, amongst other things, by a high rate of renal cell carcinomas in patients. These carcinomas occur early, around 30-40 years. The genetic analysis of patients has facilitated discovery of a tumour suppressing gene, the VHL gene (chromosome 3p), which is inactive in these patients. Subsequently, research has allowed to be shown that this gene was also inactive in the majority of the patients affected by a non-family (so-called sporadic) renal cell carcinoma, i.e. in the general population (Motzer et al., New Engl. J. Med., 335: 865-875, 1996; Vogelzang et al., Lancet, 352: 1691-1696, 1998).

Thus, the authors of the present invention have found that, in vitro on various well-characterised cell lines derived from human CCC, PTHrP and RPTH1 are expressed and the blockage of the PTHrP/RPTH1 system with antibodies directed against PTHrP or with a competitive antagonist of RPTH1 greatly inhibits cell proliferation, measured by the number of cells and by the incorporation of bromodeoxyuridine, or BrdU. In fact, these inhibition rates vary from 20% to 70% according to the used cell line and inhibitor, an effect which appears to be the consequence of a double effect of anti-proliferation and stimulation of tumour cell death.

In addition, in vivo, the effectiveness of a treatment blocking the PTHrP/RPTH1 system with a competitive antagonist of RPTH1 or with an anti-PTHrP antibody has been assayed in the nude immunodeficient mouse. This is an animal model which tolerates the implantation of human tumours allowing to test the effectiveness of compounds against tumour growth and metastasis formation. This implantation can be performed sub-cutaneously (non-invasive implantation) or in the so-called "orthotopical" way (invasive implantation with metastatis formation), i.e. with regard to the kidney directly below the renal capsule. After sub-cutaneous implantation of human tumours, the results show that the treatment over a period of 25 days by the RPTH1 antagonist or the anti-PTHrP antibody blocks the growth of the implanted tumours. Daily treatment with the anti-PTHrP antibody allowed to obtain a complete regression for 70% of the implanted tumours and a partial regression of 50% to 80% of the remaining tumours over a period of 17 days in the nude mouse.

It is important to note that the experiments also show that the expression of PTHrP is a direct or indirect target of the product of the tumour suppressing gene VHL (for Von Hippel-Lindau), a defective gene in the family forms of CCC (Von Hippel-Lindau disease) and in the majority (75%) of the sporadic CCC (as opposed to family). Within this regulation framework, the absence of active VHL in the tumour cells leads to an over-expression of PTHrP. The fundamental biological activity of VHL is the degradation, in normoxic condition and via the proteasome, of the factor HIF-1 $\alpha$ (hypoxic-induced factor) which regulates, at transcriptional level, the expression of the genes involved in the cell response to hypoxia, such as VEGF, erythropoietin and factors of cell growth and differentiation. The consequences of a defective expression of VHL are therefore cell de-differentiation, increased cell proliferation and synthesis of angiogenic factors responsible in particular of hypervascularisation of CCC. The importance of the link existing between the expression of VHL and PTHrP is thus easily understood.

The present invention describes more specifically a system using RPTH1 antagonists to block the growth of the tumour cells of renal carcinoma with clear cells in humans, in vitro and in vivo.

Kidney cancer ranks in third position among the cancers of the urogenital system after those of the prostate and the bladder. CCC is more frequent in men than in women with an incidence peak between 50 and 70 years. As explained above, its incidence is constantly increasing and explains around 2% of deaths due to cancer in France and in the world. The mortality rate is around 30% but the tumour stage currently remains the best prognostic factor. The survival rate for 5 years is 70% in the case of purely intrarenal tumours. This rate falls to 5% in the case of metastatic developments (lung, liver essentially) which occurs in almost 30% of the cases because of the latent and relatively asymptomatic character of CCC. One of the fundamental characteristics of these tumours is their resistance to all the therapies currently available including hormone therapy, radiotherapy, chemotherapy and immunotherapy. Thus, in case of metastatic kidney cancers, chemotherapy and treatments designed to stimulate immune defences (like interleukins and interferons) give deceiving results with responses not exceeding 15% and with very deleterious secondary effects on patients.

The present invention therefore proposes new therapy based on the use of PTHrP antagonists to treat patients affected by CCC, optinally before and/or after nephrectomy (recommended in CCC, whatever the tumour stage), particularly for inhibiting the growth of the primary tumour and the growth and/or development of associated metastasis, or even for promoting the regression of tumours and metastasis.

Studies of PTHrP antagonists on animals—mouse, rat and dog—in a certain number of publications do not appear to show deleterious effects upon the vital functions, therefore presenting the advantage of foreseeing a certain innocuousness of these components.

Thus, the object of the present invention is the use of at least one PTHrP antagonist in the preparation of a pharmaceutical composition for treating, in a preventative or curative way, kidney cancer, in particular renal cell carcinoma (RCC), in mammals, and in particular in human subjects.

It relates in particular to the use of at least one PTHrP antagonist for treating papillary carcinoma (chromophiles), chromophobe cell carcinoma, Bellini carcinoma or non-classified renal cell carcinomas of CCC. Preferably these components allow to treat clear cell carcinoma (CCC).

Advantageously, the present invention is of particularly great interest for inhibiting or decreasing tumour growth and/or metastasis formation in kidney cancer and/or its metastatic developments, in particular in the lung and the liver. This inhibition or this decrease can lead, for a high percentage, to a complete regression of tumours and metastasis associated with kidney cancer.

Advantageously, it is a pharmaceutical composition for the (curative) treatment or the (preventive) prophylaxis of kidney cancer.

Solid malignant tumours are distributed across carcinomas (95%) and sarcomas (5%). The development of carcinomas and sarcomas is correlated with the development of a tumoral vascularisation of tumours, referred to as angiogenesis. Any inhibition of this tumoral angiogenesis facilitates regression or at least suspension or delaying of the development of tumours. It has been found in a surprising way that anti-PTHrP antibodies and/or RPTH1 antagonists not only have an effect on tumours but also on the angiogenesis.

The pharmaceutical compositions according to the invention can be used in particular for the treatment of malignant tumours of kidney cancer, more specifically the treatment of solid malignant tumours.

They can also be used to partially or completely inhibit the tumour angiogenesis.

The invention also relates to a method of treatment of kidney cancer, in particular clear cell carcinomas, comprising the administration to a subject, in particular human, of an effective dose of a PTHrP antagonist or a pharmaceutical composition containing it.

In the present invention, the term "a PTHrP antagonist" includes any compound decreasing the biological effect or effects of PTHrP, in particular those described above. A compound corresponds to a compound or to a mixture of compounds.

This compound can be in particular a compound binding the PTHrP receptor inhibiting partially, or even totally, the binding of PTHrP to its receptor. Preferably, this compound is an antagonist of the PTHrP receptor and preferably a competitive antagonist of PTHrP. These antagonists include peptides of PTH or PRHrP comprising a substitution or deletion of at least one amino acid of the sequence of the PTH and of the PTHrP, or a partial sequence of the PTH or PTHrP peptides, optionally comprising a substitution or a deletion of at least one amino acid of their sequence. Specific examples of antagonist compounds binding the PTHrP receptors include PTHrP (3-34), PTHrP (7-34), PTHrP (8-34), PTHrP (9-34), PTHrP (10-34), the amides or variants thereof. Variants present a replacement, a deletion or an addition of at least one amino acid such as in particular (Asn10, Leu11, D-Trp12) PTHrP (7-34) amide (human or murine). Furthermore, among the above-described polypeptides, are also included those which present a deletion, a substitution, an addition or an insertion of at least one amino acid of the peptide sequence of PTH or PTHrP and which have an antagonist activity in respect of PTHrP. It is also possible to mention a derivative of TIP (tuberoinfundibular peptide) as a PTHrP antagonist, such as truncated peptides of TIP(1-39) (tuberoinfundibular peptide 1-39), in particular TIP(7-39) and its derivatives which have been described as powerful RPTH1 antagonists (Hoare et al, Peptides 23: 989-998, 2002).

According to another embodiment of the present invention, the PTHrP antagonist can be a non-peptidic compound which decreases the biological effect or effects of PTHrP.

The PTHrP antagonist can also be a compound binding a ligand of the PTHrP receptor, thereby partially or even totally inhibiting the binding of PTHrP to its receptor. This compound can be selected from anti-PTHrP antibodies and, more preferably, a humanised anti-PTHrP antibody.

According to a particular aspect of the invention, the PTHrP antagonist can be a compound increasing the presence of active VHL, thereby decreasing the biological effect or effects of PTHrP. Within this context, this compound can be the product of the tumour suppressing gene VHL, which can be obtained in particular by gene therapy.

Besides, the PTHrP antagonist can also be a compound reducing the expression of PTHrP. This compound binds mRNA or gene of PTHrP, inhibiting, partially or even totally the expression of PTHrP. This compound can be for example an antisense oligonucleotide of PTHrp, a RNAi, a transcription factor repressing the expression of the PTHrP gene or a compound decreasing the stability of the mRNA of PTHrP.

The present invention also includes the possibility of using several kinds of PTHrP antagonists such as defined above for the treatment of kidney cancer. Thus, the present invention includes for example a method of treatment including gene therapy such as described above and the administration of a PTHrP antagonist such as an antagonist of the PTHrP receptor or an anti-PTHrP antibody.

In the present invention, the term "a PTHrP receptor" includes a receptor binding PTHrP and includes in particular the PTH/PTHrP receptor of type I (referred to as RPTH1).

The term "ligand" includes a compound binding an enzyme or a receptor.

The term "a compound binding a ligand of a PTHrP receptor inhibiting the binding between the ligand and the receptor" includes a compound (e.g., an anti-PTHrP antibody) which inhibits the binding of a ligand (e.g., PTHrP) to a PTHrP receptor through the binding to said ligand of the PTHrP receptor. Examples of anti-PTHrP antibodies include antibodies such as a humanised antibody, a human antibody, a chimeric antibody, an antibody (such as the antibody #23-57-137-1) obtained from a hybridoma (such as the hybridoma #23-57-137-1) or a fragment of these antibodies and/or a modified form of said fragment. The antibody can be polyclonal, but preferably is monoclonal.

The term "a humanised antibody" includes an antibody comprising a part derived from a human antibody and complementary determinant regions (CDRs) derived from an antibody other than human (e.g. murine antibody).

The antibody used in the present invention can be produced through methods known to the man skilled in the art. Preferably, the anti-PTHrP antibody is a monoclonal antibody derived from a mammal.

This antibody includes in particular those produced by a hybridoma and those produced by genetic engineering using host cells transformed with a recombinant expression vector carrying a gene encoding the antibody. The antibody can bind PTHrP and prevent the binding of the PTHrP to its receptor, thus blocking the transduction signal of PTHrP and consequently inhibiting the biological activity of PTHrP.

By way of examples, mention can be made in particular of the anti-PTHrP(1-34) antibodies (human, rat) of Bachem (Bachem Biochimie Sarl, Voisins-le-Bretonneux, France), the anti-PTHrP(34-53) antibody (Ab-2, human) of Oncogene (France Biochem, Meudon, France), the antibody #23-57-137-1 (described in particular in the patent application EP1197225) and the anti-PTHrP(107-139) antibody (human) obtained by conventional methods of antibody preparation.

The hybridoma producing monoclonal antibodies can be obtained as following: PTHrP is used as antigen for immunisation according to conventional methods of immunisation. The resulting immunocytes are fused with known parent cells according to conventional cell fusion methods and the cells producing the antibodies are thus screened from fused cells by conventional screening methods.

The human PTHrP used as antigen agent for producing antibodies is prepared by expression of the sequence of the PTHrP gene described by Suva, L. J. et al., Science, 237, 893, 1987. A nucleotidic sequence encoding PTHrP is inserted in a known expression vector and a suitable host cell is transformed with this expression vector. PTHrP protein is then isolated and purified from transformed host cells or from the supernatent obtained using transformed host cells by conventional methods. The obtained PTHrP protein is used as antigen.

According to another embodiment of the invention, a peptide corresponding to a partial sequence of the PTHrP peptide can be chemically synthesised and used as antigen. In particular, a partial sequence of 34 amino acids of the N-terminal region of the peptidic sequence of PTHrP can be chemically synthesised and used as antigen.

The mammal to be immunised with this antigen can be of any type. The mammal is preferably chosen in taking into account the compatibility with the parent cell used for the fusion. A rodent (e.g. mouse, rat or hamster), a rabbit or a monkey are generally used.

The immunisation of the mammal with the antigen can be performed by any known method, for example by intra peritoneal or subcutaneous injection of the antigen into the mammal. More specifically, the antigen is diluted appropriately in a phosphate buffer (PBS) or a physiological saline solution, wherein the resulting dilution or suspension is then mixed in appropriate quantity with a conventional adjuvant (e.g., Freund's complete adjuvant) in order to obtain an emulsion. The emulsion is injected into the mammal several times at intervals of 4 to 21 days. The antigen can possibly be attached to an appropriate support.

After immunisation, the antigenic level of the serum is assayed. When the desired level is obtained, the immunocytes are isolated from the mammal and fused. The preferred immunocyte used is a splenic cell.

The parent cell used for the fusion is a myeloma cell derived from a mammal. This cell can be any known cell line and is for example P3 (P3x63Ag8.653) (J. Immunol. 123, 1548-1550, 1979), P3x63Ag8U.1 (Current Topics in Microbiology and Immunology 81, 1-7, 1978), NS-1 (Kohler, G. and Milstein, C. Eur. J. Immunol., 6, 511-519, 1976), MPC-11 (Margulies, D. H. et al., Cell, 8, 405-415, 1976), SP2/0 (Shulman, M. et al., Nature, 276, 269-270, 1978), FO (de St. Groth, S. F. et al., J. Immunol. Methods, 35, 1-21, 1980), S194 (Trowbridge, I. S., J. Exp. Med., 148, 313-323, 1978) or R210 (Galfre, G. et al., Nature, 277, 131-133, 1979).

The fusion is performed by any known method such as the method of Milstein et al. (Kohler, G. and Milstein, C., Methods Enzymol., 73, 3-46, 1981). In particular, the fusion is performed in a conventional culture medium in the presence of a cell fusion promoter. The fusion promoter can be polyethylene glycol (PEG) or a virus known for this purpose such as the virus of Sendai (hemagglutinating virus of Japan; HVJ). If necessary, in order to improve the effectiveness of the fusion, an additive can be incorporated such as dimethyl sulphoxide.

The ratio between the immunocyte cells and the myeloma can vary to a large range. By way of illustration, immunocytes can be present in an amount 1 to 10 times greater than the cells of the myeloma. The culture medium used for the fusion is for example the RPMI 1640 or MEM medium appropriate for the growth of myeloma cell lines or any other medium conventionally used for the culture of cell lines. An additional serum can be added to the medium such as foetal calf serum (FCS).

The fusion is thus performed by mixing the two cell types in a culture medium, preferably by adding a PEG solution to the medium, generally at a concentration of 30-60% (w/v). The solution is then mixed, thus producing the desired fused cells, hydridomas. An appropriate culture medium is then added to the obtained solution and the whole is centrifuged in order to remove the supernatant. The obtained hybridomas are selected by culture in a conventional selective medium such as hypoxanthine-aminopterin-thymidine (HAT) medium in order to suppress the non-desired (non-fused) cells. A method of dilution is then implemented in order to screen and clone the hybridomas which secrete the desired antibody.

According to a variation for antibody production not using the technique of hybridomas, immunisation of a human mammal with the antigen such as described above can be performed. In particular, a human lymphocyte can be immunised with PTHrP in vitro, then fused with an immortalised human myeloma cell, thus producing a human antibody binding PTHrP. According to another embodiment, a human antibody directed against PTHrP can be prepared through injection of PTHrP as antigen into a transgenic animal with the full repertoire of the genes of human antibodies in order to produce cells producing anti-PTHrP antibodies, then by immortalisation of the resulting cells. The immortalised cells thus prepared produce the expected human antibody. This method is described in detail in the following patents (WO 96/33735; EP 822 830; U.S. Pat. No. 6,150,584).

Recombinant antibodies can also be used. The recombinant antibodies can be prepared by cloning a gene encoding the antibody from the hybridoma, by inserting the gene into an appropriate vector and iby ntroducing the vector into a host cell in order to produce the antibody using this host cell according to conventional recombinant DNA technologies (Vandamme, A. M. et al., Eur. J. Biochem., 192, 767-775, 1990).

In the present invention, an artificially modified recombinant antibody can also be used, in particular for decreasing the heterogeneity against the human body. Chimeric or humanised antibodies can thus be used. These modified antibodies can be produced by known methods.

The antibody used in the present invention can be a fragment of an antibody or a modified form of this fragment; these compounds must bind PTHrP and inhibit the biological activity of PTHrP. Thus, antibody fragments are included such as Fab, Fab'2, CDRs, etc. or single chain (ScFv).

The fragments of antibodies can be produced by preparing genes for these fragments and expressing them in appropriate host cells.

A modified form of an antibody such as described above can also be used, for example an anti-PTHrP antibody conjugated with a molecule such as polyethylene glycol. The modified antibodies can be prepared through chemical modification of the antibodies such as described above. These chemical modifications are known to the man skilled in the art.

For the production of the antibodies used in the present invention, any expression system can be used such as an eukaryotic or prokaryotic cell system. Eukaryotic cells include the established cell lines (e.g. mammals, insects, mushrooms and levures). Procaryotic cells include bacteria such as the *E. Coli* bacteria.

Preferably, the antibody used in the present invention is expressed in a mammal cell such as CHO, COS, myeloma, BHK, Vero or HeLa cells.

The transformed host cell is cultivated in vitro or in vivo in order to produce the antibody of interest. The host cells are cultivated in an appropriate conventional medium. The culture medium can be selected from the following medium: DMEM, MEM, RPMI 1640 or IMDM. The culture medium can further include an additional serum such as foetal calf serum (FCS).

The antibody expressed and produced as described above can be isolated from the cells or the host animals and purified by any known method, in particular using an affinity column. Any other known method for isolating and purifying antibodies can be used alone or in combination, in particular chromatographs using columns, by methods of filtration, ultrafiltration or dialysis.

The determination of the antigenic or inhibiting activity of the antibodies thus prepared can be performed by using any method known to the man skilled in the art, such as the following methods: ELISA (enzyme-linked immunosorbent assay), EIA (enzyme immunoassay), RIA (radioimmunoassay) or the methods using a fluorescent antibody.

The pharmaceutical compositions according to the invention advantageously include one or several pharmaceutically acceptable excipients or carriers. It is possible to cite for example saline, physiological, isotonic, buffered solutions, etc., which are pharmaceutically acceptable and known by the man skilled in the art. The compositions can contain one or several agents or carriers selected from dispersants, solubilizing agents, stabilizers, preservatives, etc. Agents or carriers which can be used in formulations (liquids and/or injectable and/or solids) are in particular methyl cellulose, hydroxymethyl cellulose, carboxymethyl cellulose, polysorbate 80, mannitol, gelatine, lactose, vegetable oils, acacia, etc. The compositions can be formulated in the form of injectable suspension, gels, oils, tablets, suppositories, powders, capsules, etc., possibly by means of galenic forms or mechanisms ensuring prolonged and/or delayed release. For this type of formulation, an agent such as cellulose, carbonates or starchs is advantageously used.

The compounds or compositions according to the invention can be administered in different ways and in different forms. Thus, they can be injected systemically or orally, preferably systemically, like for example by intravenous, intramuscular, subcutaneous, transdermic, intra-arterial means, etc. For the injections, the compounds are generally formulated in liquid suspensions which can be injected by means of syringes or perfusions, for example. It is understood that the flow and/or the dose injected can be adapted by the man skilled in the art depending upon the patient, the pathology, the mode of administration, etc. Typically the compounds are administered at doses which can vary between 0.1 pg and 500 mg/kg of corporal weight, more generally from 0.01 to 10 mg/kg, typically between 0.1 and 10 mg/kg. In addition, repeated injections can be performed, if appropriate. Otherwise, the compositions according to the invention can further include other agents or active principles.

LEGENDS OF THE DRAWINGS

FIG. 1: schematic diagram representing the PTHrP gene and its isoforms.

Figure 2:
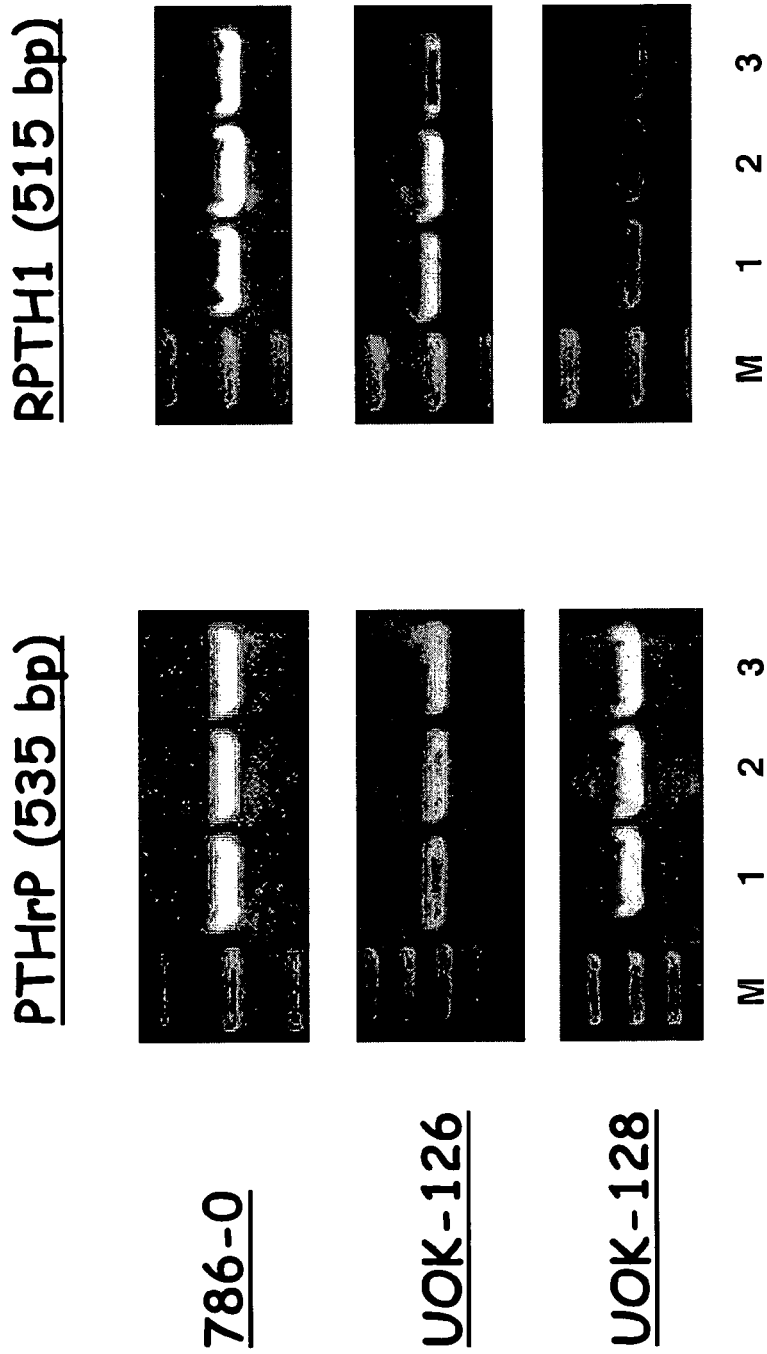

FIG. 2: gels showing the expression of PTHrP and RPTH1 at the level of the mRNA in 3 samples (numbered 1, 2 and 3) for 3 tumor cell lines 786-0, UOK-126 and UOK-128. Experiments performed by RT-PCR.

Figure 3A:
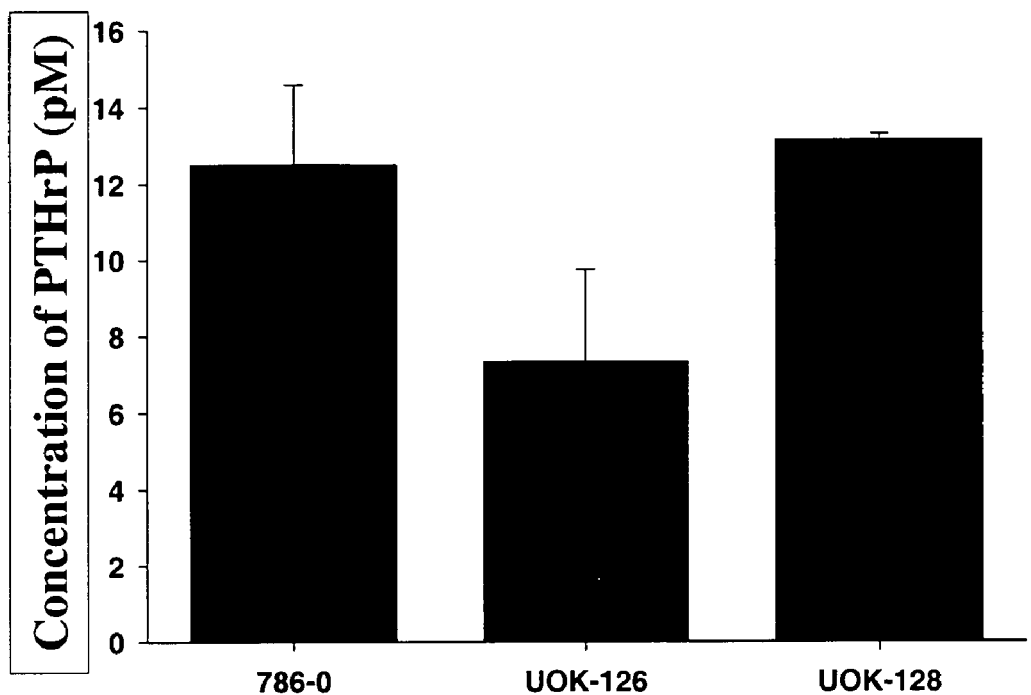

FIG. 3: FIG. 3A: Dosage of PTHrP protein by a radio-immunological method in the conditioned medium of the 3 tumor cell lines 786-0, UOK-126 and UOK-128 using an antibody binding specifically the amino-terminal part of PTHrP.

Figure 3B:
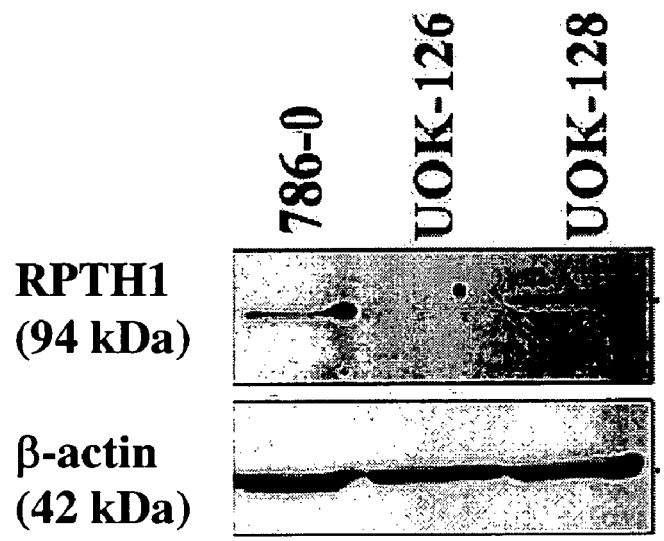

FIG. 3B: Measurement of the expression of RPTH1 by Western blot in the 3 tumor cell lines 786-0, UOK-126 and UOK-128 with an antibody directed against RPTH1.

Figure 4:
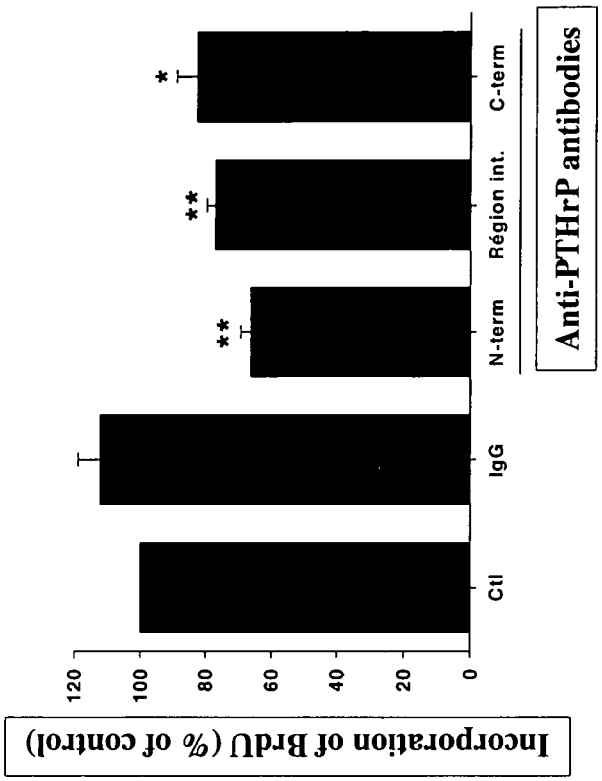
Figure 4:
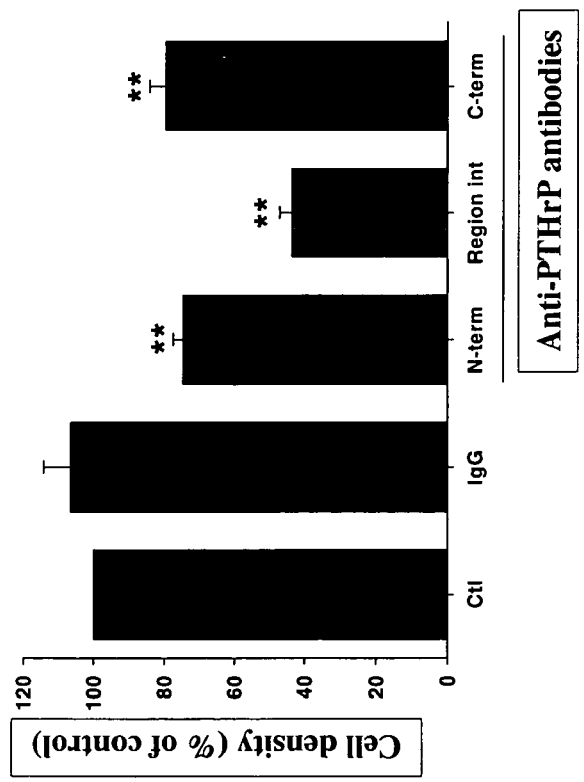

FIG. 4: FIG. 4 shows the effect of the antibodies directed against the various regions of PTHrP on the proliferation of the tumour cells 786-0 in vitro measured by the number of cells (on the left) and by the incorporation of BrdU (on the right).

Figure 5:
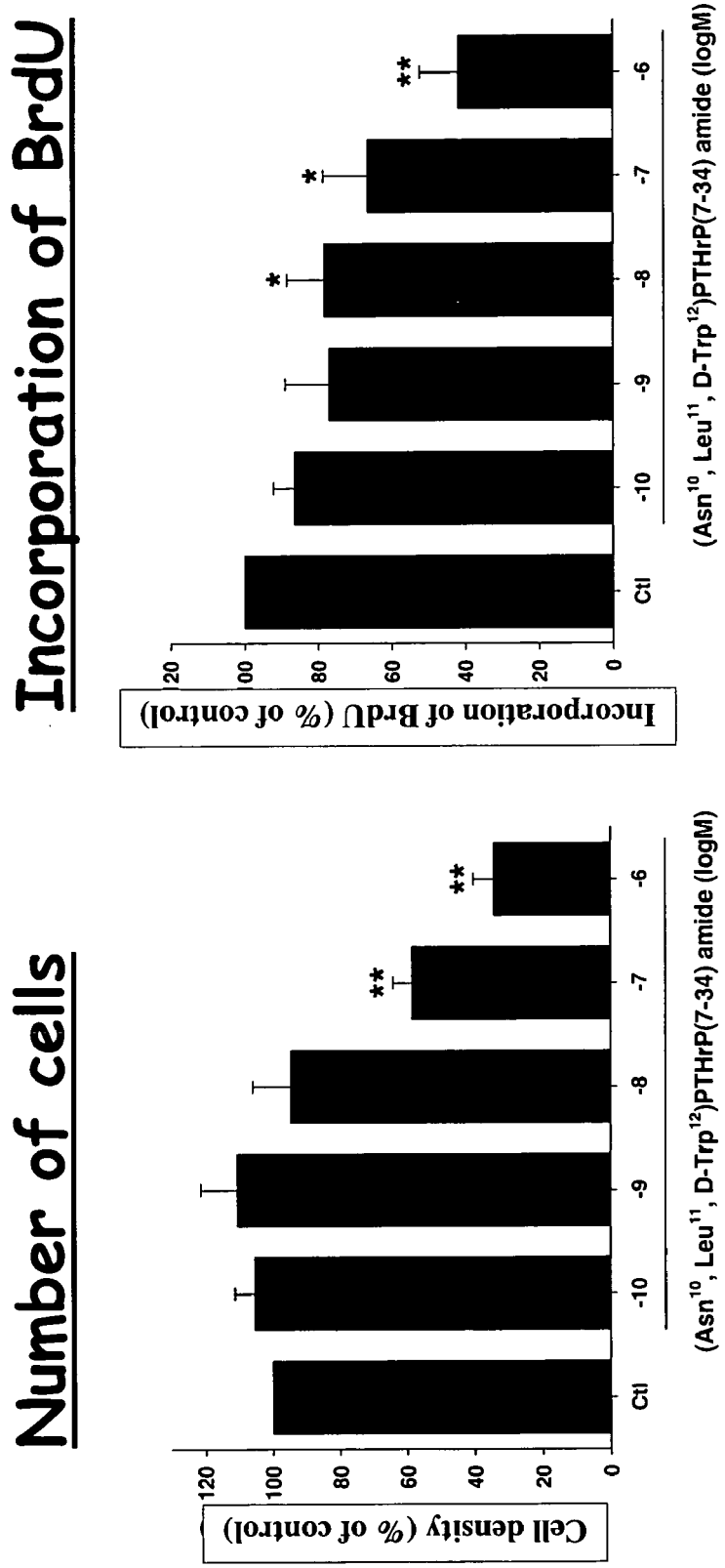

FIG. 5: FIG. 5 shows the effect of the RPTH1 antagonist, (Asn10, Leu11, D-Trp12)hPTHrP(7-34) amide (h pour human) at different concentrations on the proliferation of the tumour cells 786-0 in vitro measured by the number of cells (on the left) and by the incorporation of BrdU (on the right).

Figure 6:
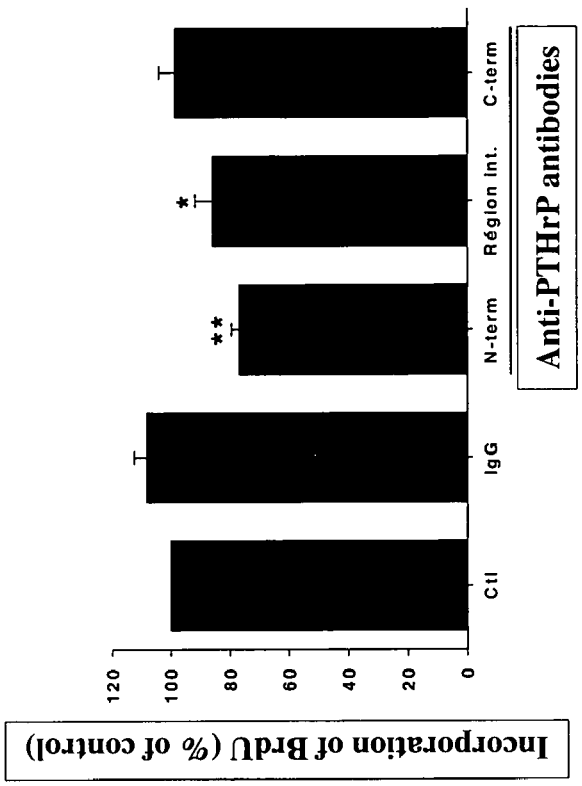
Figure 6:
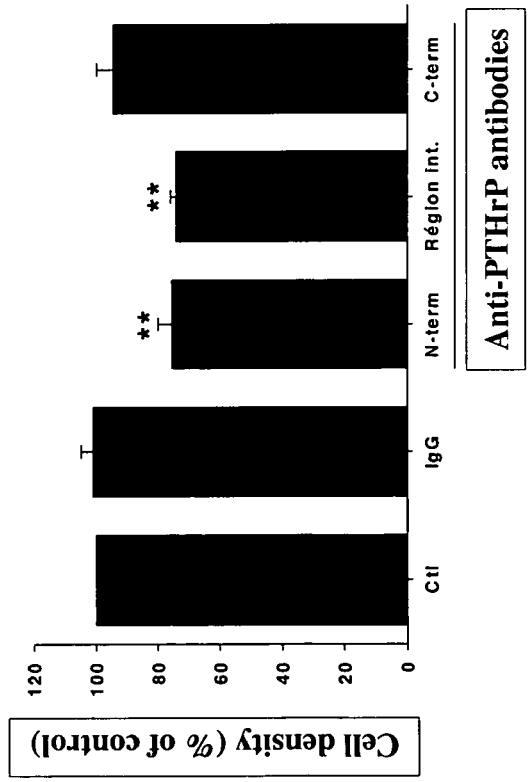

FIG. 6: FIG. 6 shows the effect of the antibodies directed against the different regions of PTHrP on the proliferation of the tumour cells UOK-126 in vitro measured by the number of cells (on the left) and by the incorporation of BrdU (on the right).

Figure 7:
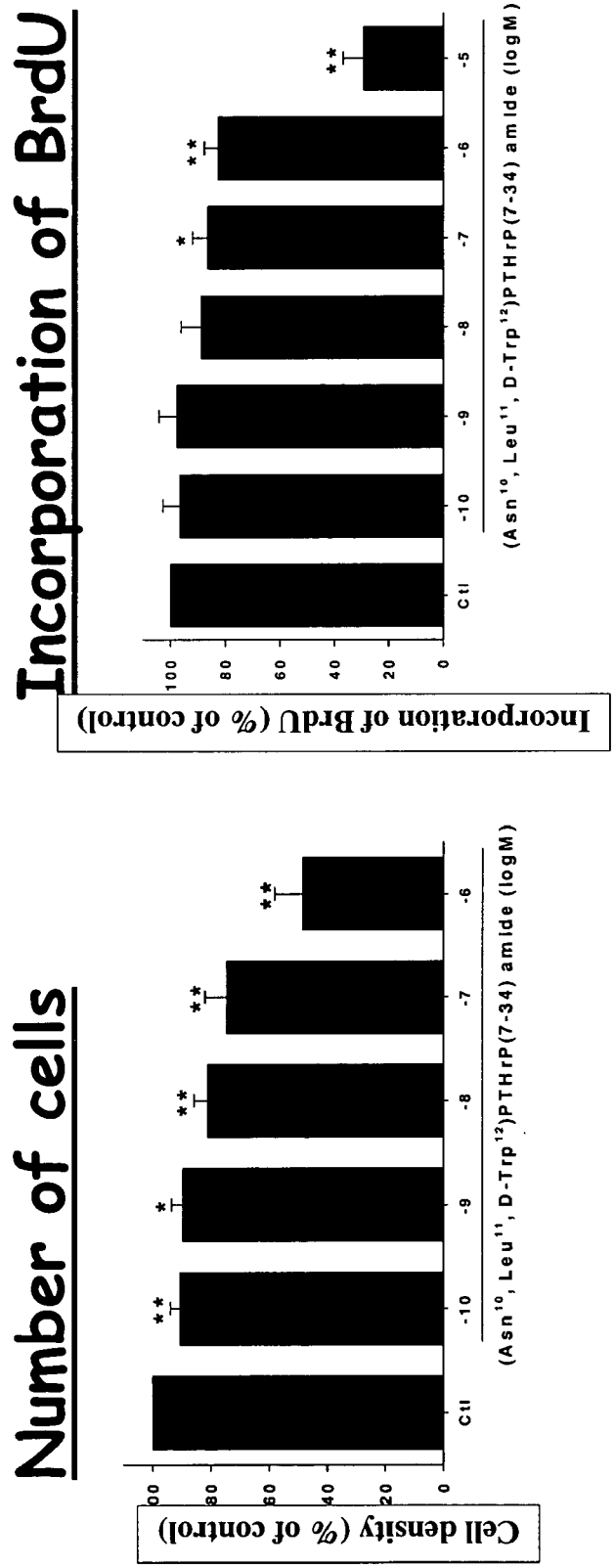

FIG. 7: FIG. 7 shows the effect of the RPTH1 antagonist, (Asn10, Leu11, D-Trp12)hPTHrP(7-34) amide at different concentrations on the proliferation of the tumour cells UOK-126 in vitro measured by the number of cells (on the left) and by the incorporation of BrdU (on the right).

Figure 8:
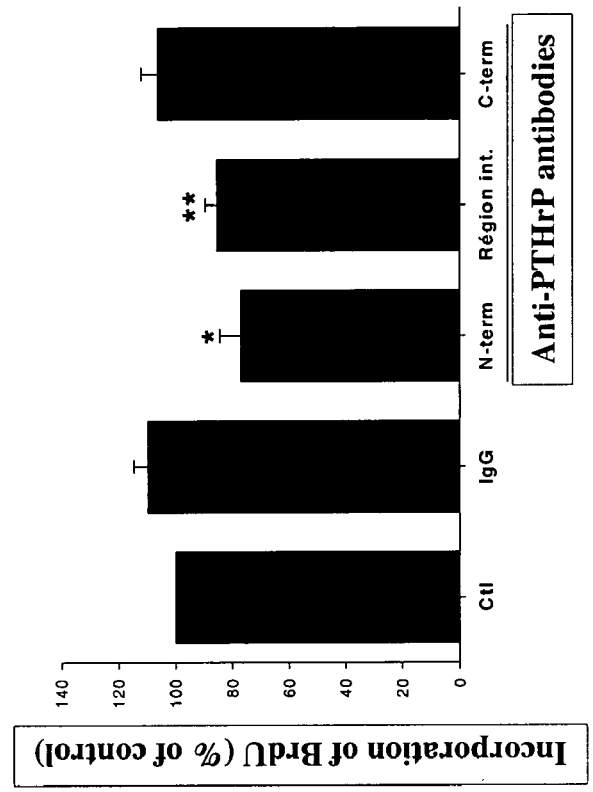
Figure 8:
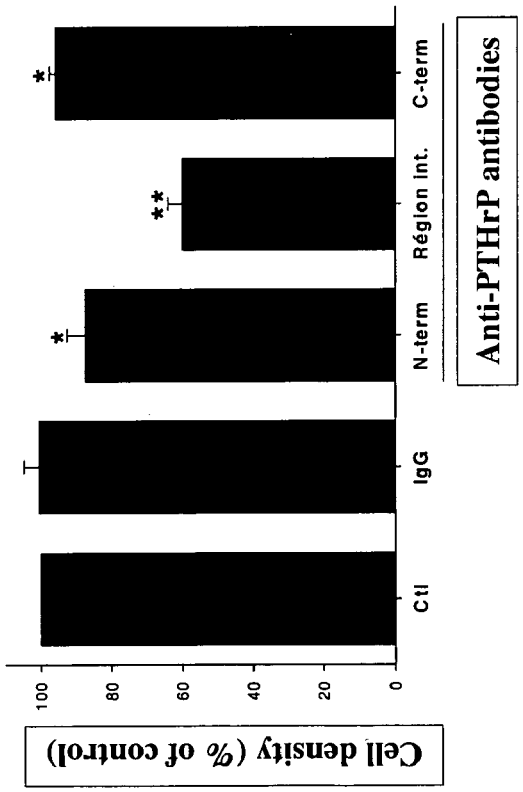

FIG. 8: FIG. 8 shows the effect of the antibodies directed against the different regions of PTHrP on the proliferation of the tumour cells U-OK-128 in vitro measured by the number of cells (on the left) and by the incorporation of BrdU (on the right).

Figure 9:
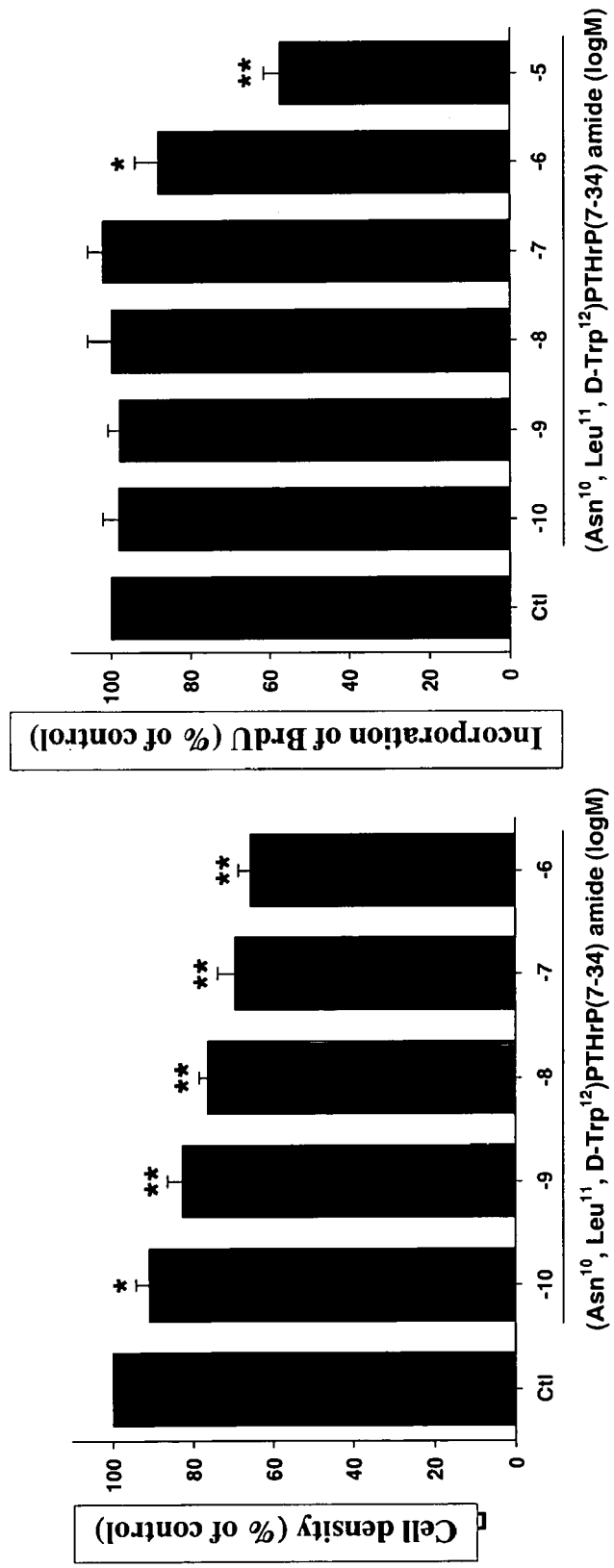

FIG. 9: FIG. 9 shows the effect of the RPTH1 antagonist, (Asn10, Leu 11, D-Trp12)hPTHrP(7-34) amide at different concentrations on the proliferation of the tumour cells UOK-128 in vitro measured by the number of cells (on the left) and by the incorporation of BrdU (on the right).

Figure 10:
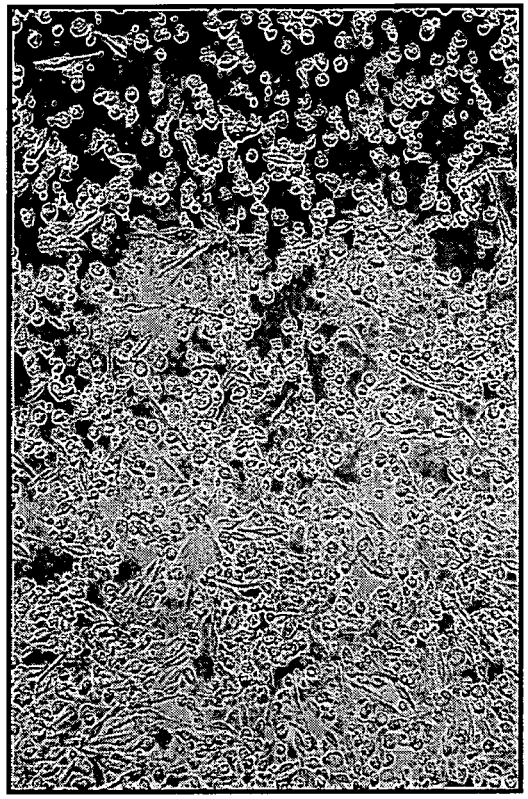
Figure 10:
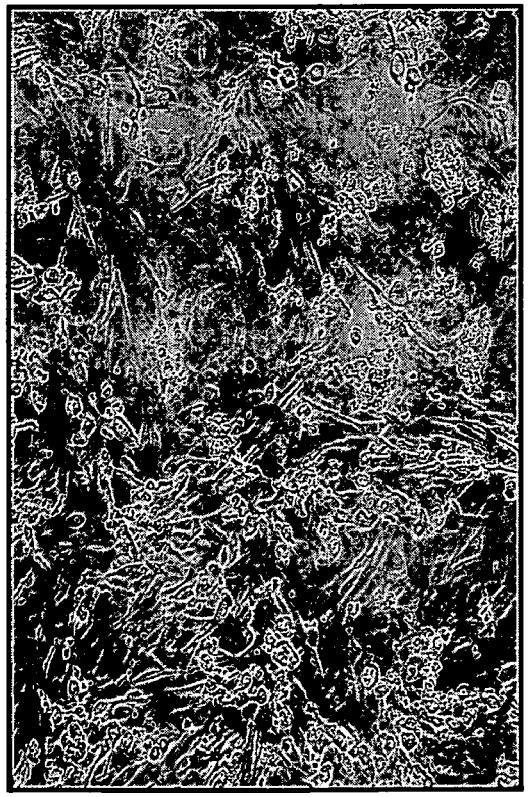

FIG. 10: A reproduction of photographs of the 786-0 cells in culture in a RPMI 1640 medium without serum (with 0.1% BSA) and treated either as a control (on the left) or in the presence of $10^{-6}$ M of the amide antagonist (Asn10, Leu11, D-Trp12)hPTHrP(7-34) (on the right) for 48 hrs.

FIG. 11: FIG. 11 shows the effect of the RPTH1 antagonist, (Asn10, Leu 11, D-Trp12)hPTHrP(7-34) amide on the apoptosis of the tumour cells 786-0.

Figure 11A:
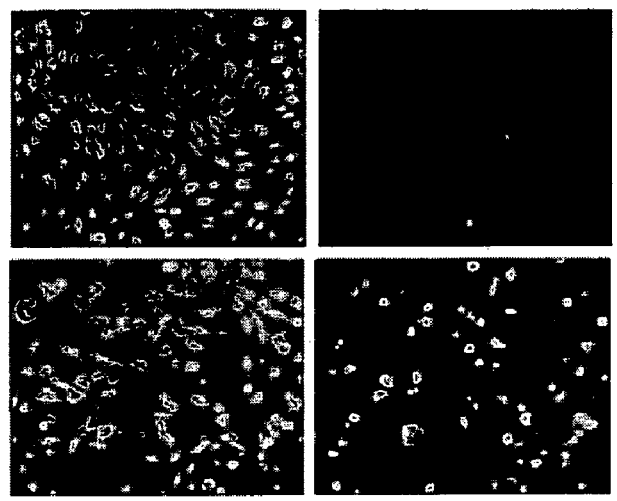

FIG. 11A: micrograph of fluorescence of the control cells (above) or the cells treated by the RPTH1 antagonist (below) with orange acridine (AO: a, c) and ethidium bromide (EB: b, d) (x 400). FIG. 11 B: DNA fragmentation test.

Figure 12:
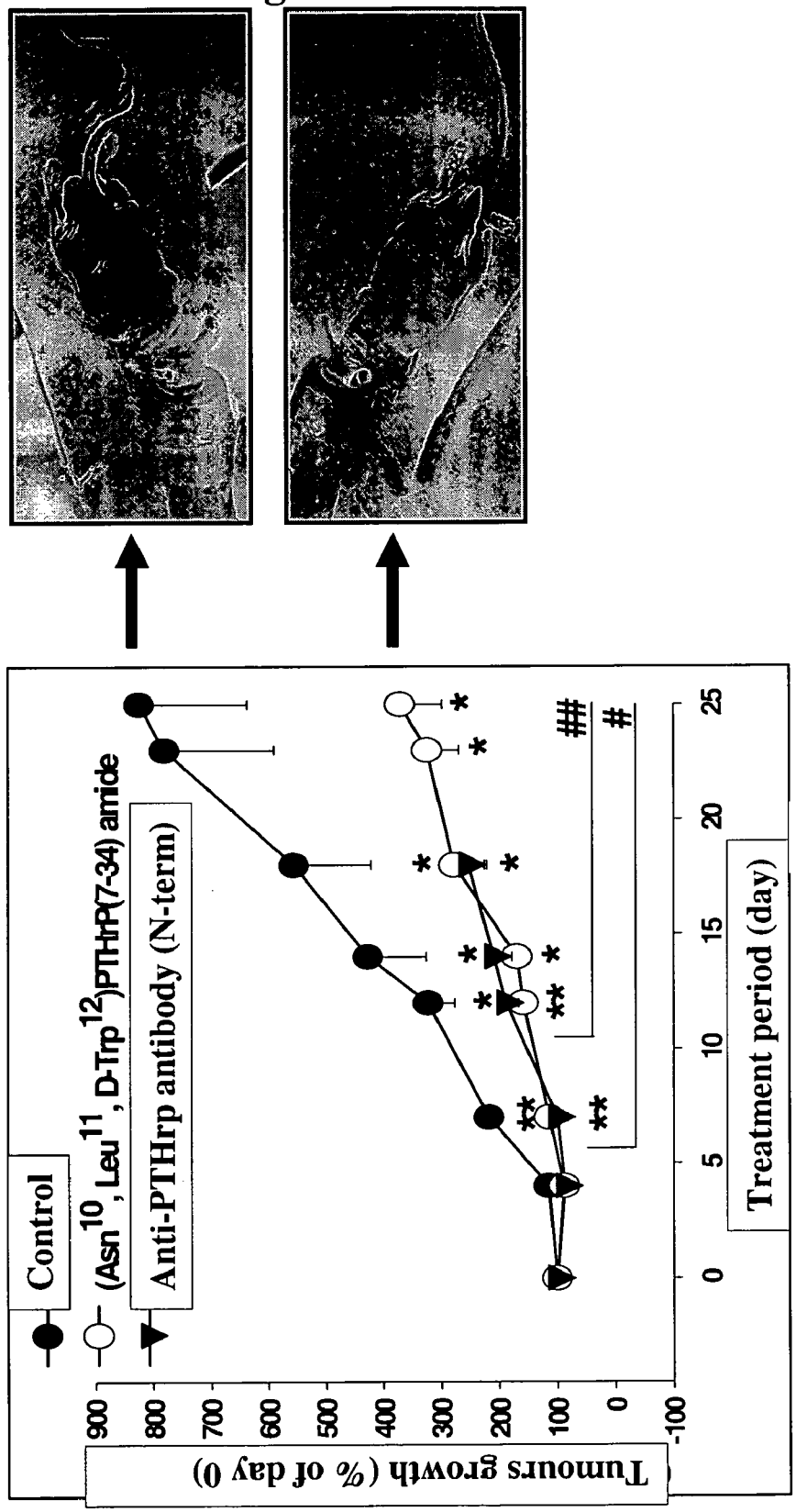

FIG. 12: FIG. 12 shows the growth of the tumours of mice treated either as a control or by the antagonist according to the protocol described in the following examples. The growth results are expressed as a percentage of the tumour volume at day 0 at the beginning of the treatments. This figure also shows the reproduction of photographs: above, a mouse treated as a control for 25 days with its very observable tumours and below, a mouse treated for 25 days by an antagonist.

Figure 13:
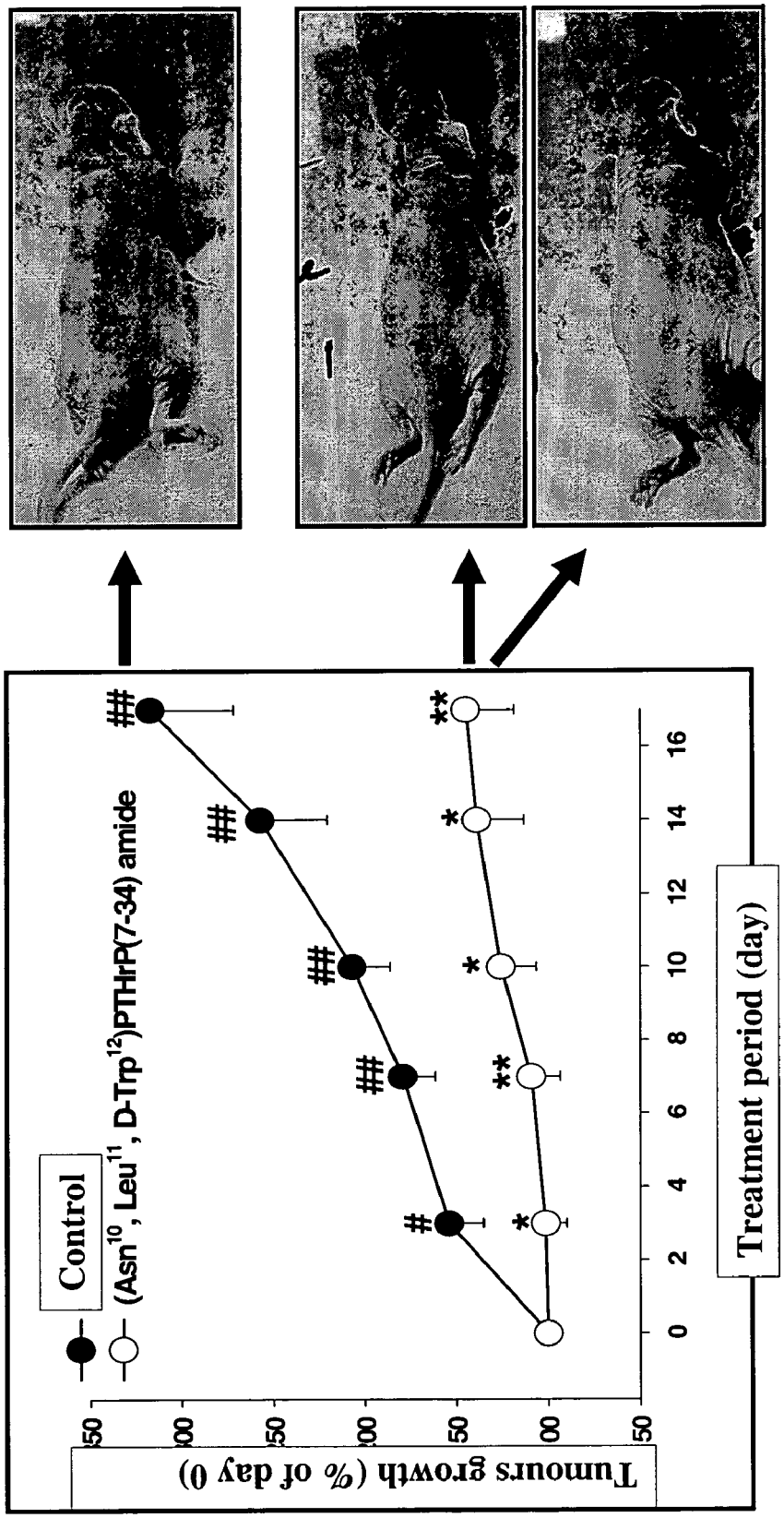

FIG. 13: FIG. 13 shows the growth of the tumours of the mice treated either as a control or by the antagonist according to the experimental protocol described below. The growth rates are expressed as a percentage of the tumour volume at day 0 at the beginning of the treatments. This figure also shows the reproduction of photographs: above, a mouse treated as a control for 17 days with its highly observable tumour and below, by way of example two mice treated for 17 days by an antagonist.

Figure 14:
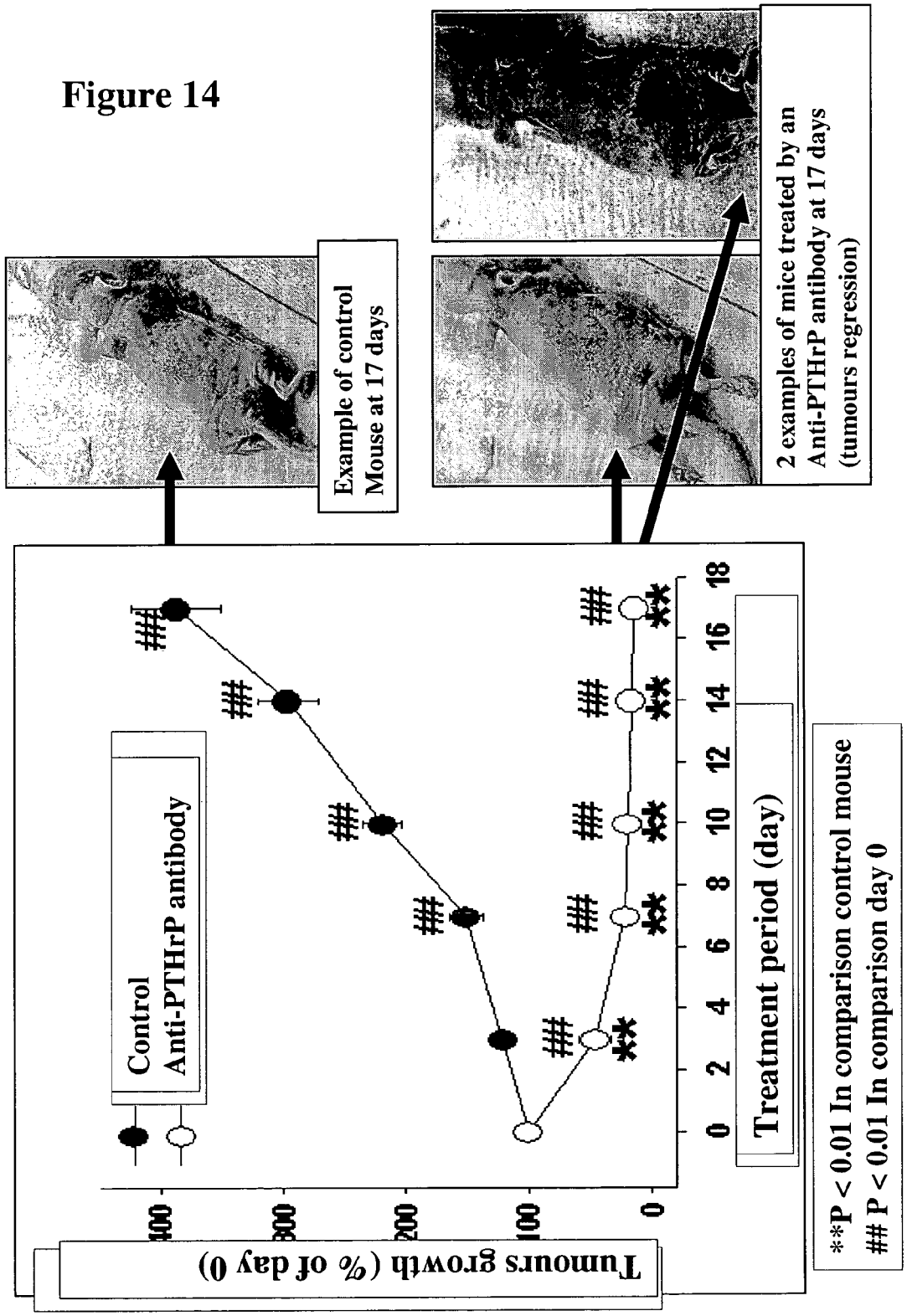

FIG. 14: FIG. 14 shows the growth of the tumours of the mice treated either by an antibody directed against the N-terminal extremity of PTHrP or by non-specific IgG according to the experimental protocol described below. The growth results are expressed as a percentage of the tumour volume at day 0 at the beginning of the treatments. This figure also shows the reproduction of photographs: above, a mouse treated as a control for 17 days with its highly observable tumour and below, by way of example a mouse treated for 17 days by an anti-PTHrP antibody (N-term).

Figure 15:
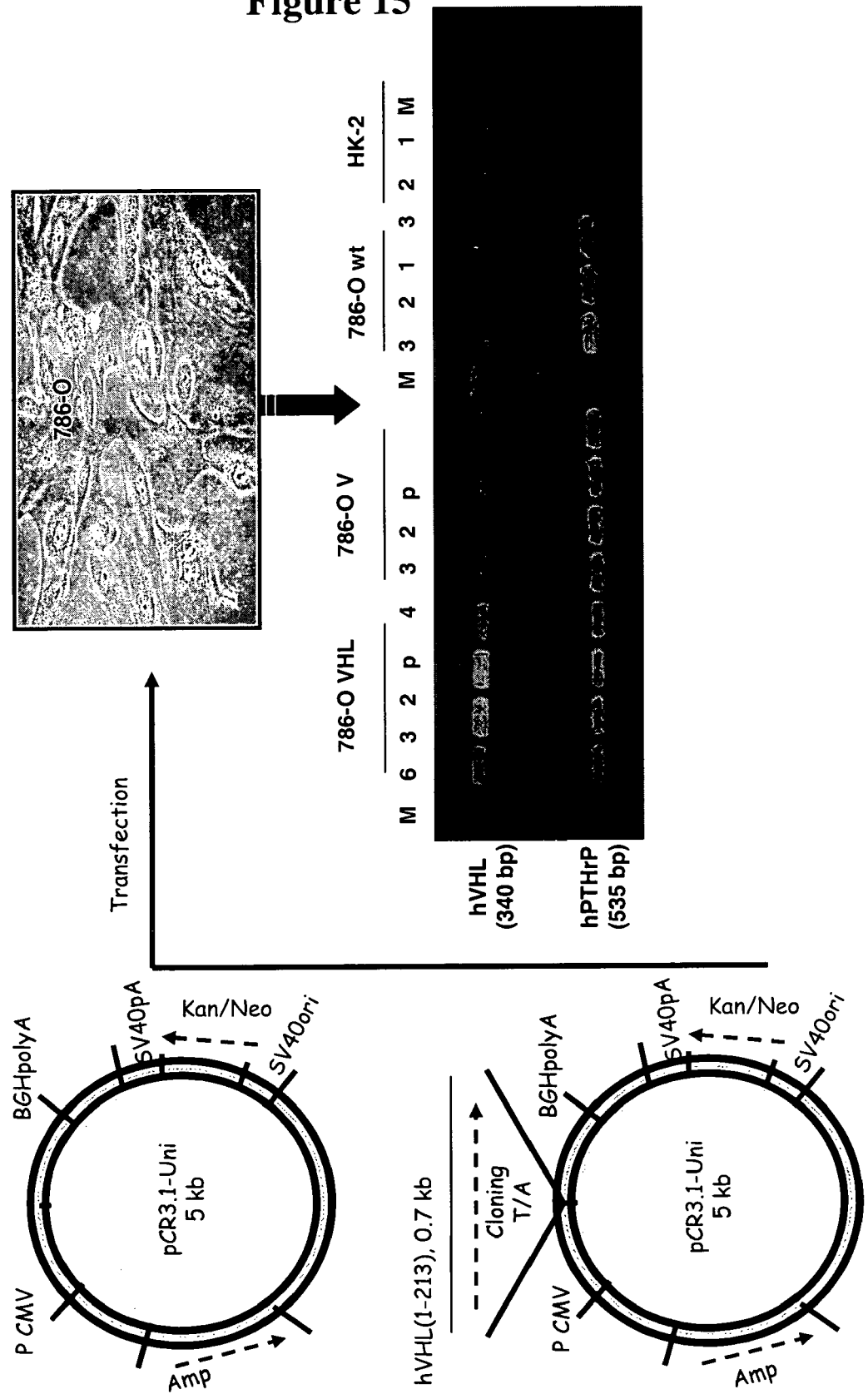

FIG. 15: Shown on the left of FIG. 15 are the vectors pCR3.1-Uni alone or encoding VHL(1-213). These vectors have been transfected into 786-0 cells (cf below). Three individual clones have been isolated after selection by G418 as well as all the clones for the cells transfected by the vector alone (786-0 V, individual clones 2, 3, 4 and mixed clones p) or by the vector encoding VHL (786-0 VHL, individual clones 2, 3 and 6 and mixed clones p). Parallel to these clones, 3 samples of non-transfected 786-0 cells (786-0 wt for "wild-type") and 3 samples of HK-2 cells (normal human proximal tubular cells) have also been tested for the expression of VHL and PTHrP. The gels of this figure represent the expression of VHL obtained by RT-PCR on total RNA isolated from the different cells (band at 340 bp) according to the protocol described below.

Figure 16:
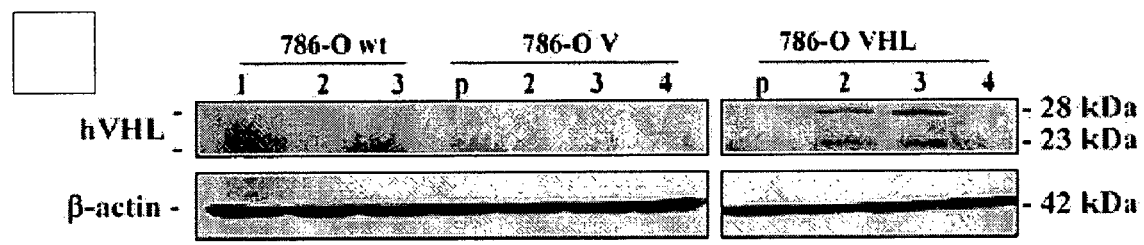

FIG. 16: Shown in this drawing are the Western Blots of the lysates of 786-0 cells which have not been transfected and those which have been transfected with the vector alone or with the coding vector encoding VHL, wherein these lysates are incubated in the presence of an antibody directed against the epitope HA (pVHL) or β-actin.

Figure 17:
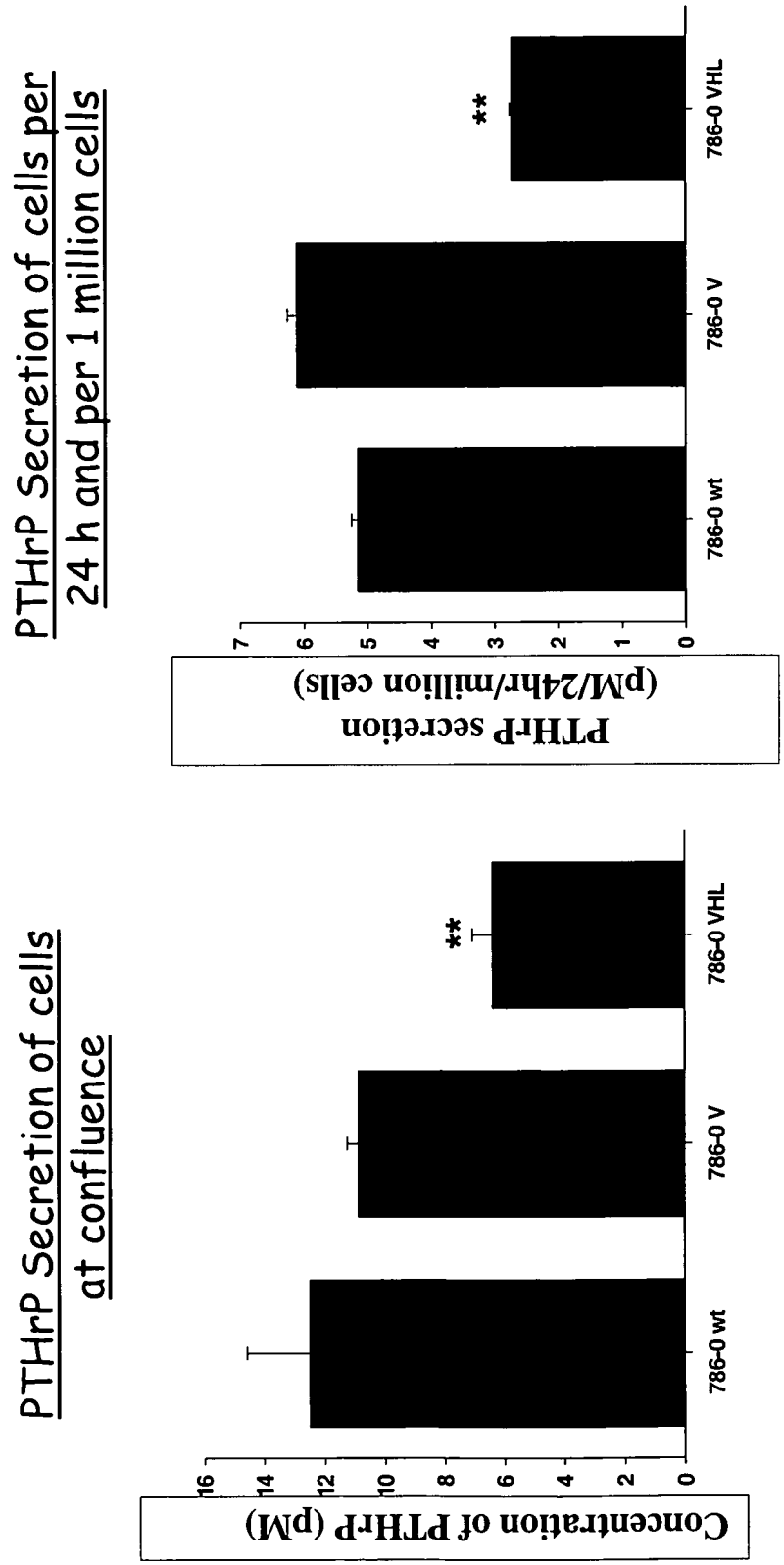

FIG. 17: FIG. 17 on the left shows by RIA of PTHrP that the production of PTHrP is decreased by 50% in the 786-0 cells which have been transfected with the vector encoding VHL (786-0 VHL) in comparison with the cells that have not been transfected (786-0 wt) or transfected with the vector alone (786-0 V). FIG. 17 on the right shows the secretion of PTHrP in pM per 24 hrs and per million cells.

Figure 18:
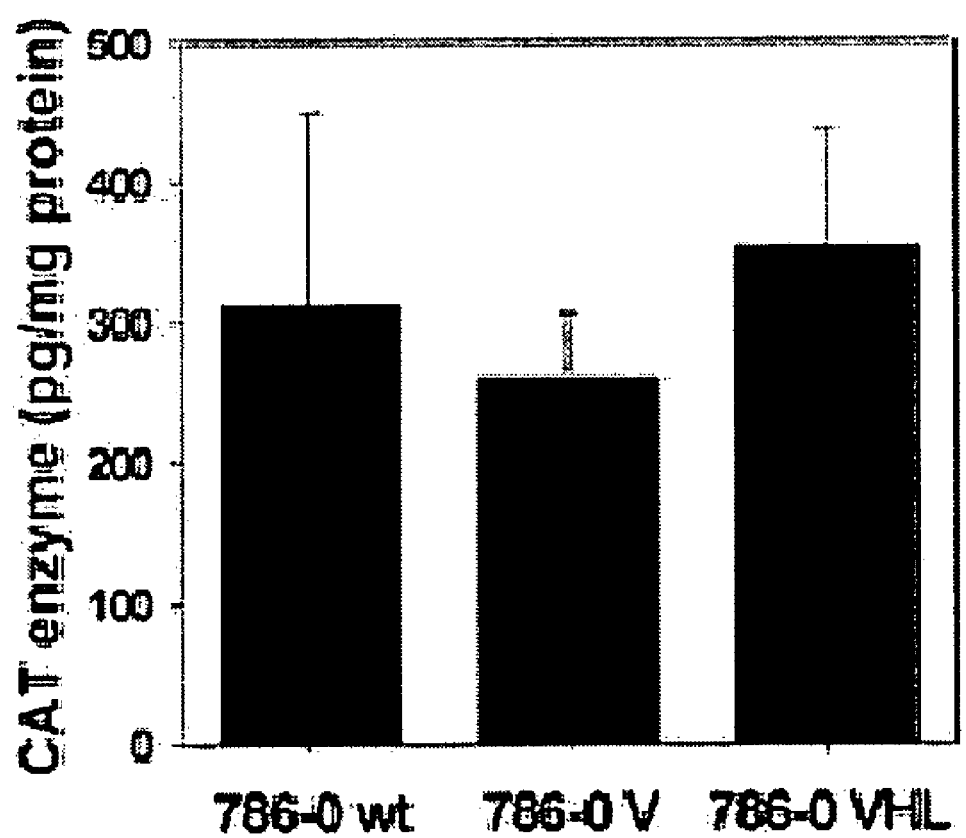

FIG. 18: Expression of CAT in the 786-0 cells that have not been transfected, the clones 3 and 4 of 786-0 cells transfected by the vector, the clones 2 and 3 of 786-0 cells transfected by the coding vector encoding VHL wherein the clones are transciently transfected with a expression plasmid encoding CAT under the control of hPTHrP promoters (hPTHrP-CAT).

Figure 19:
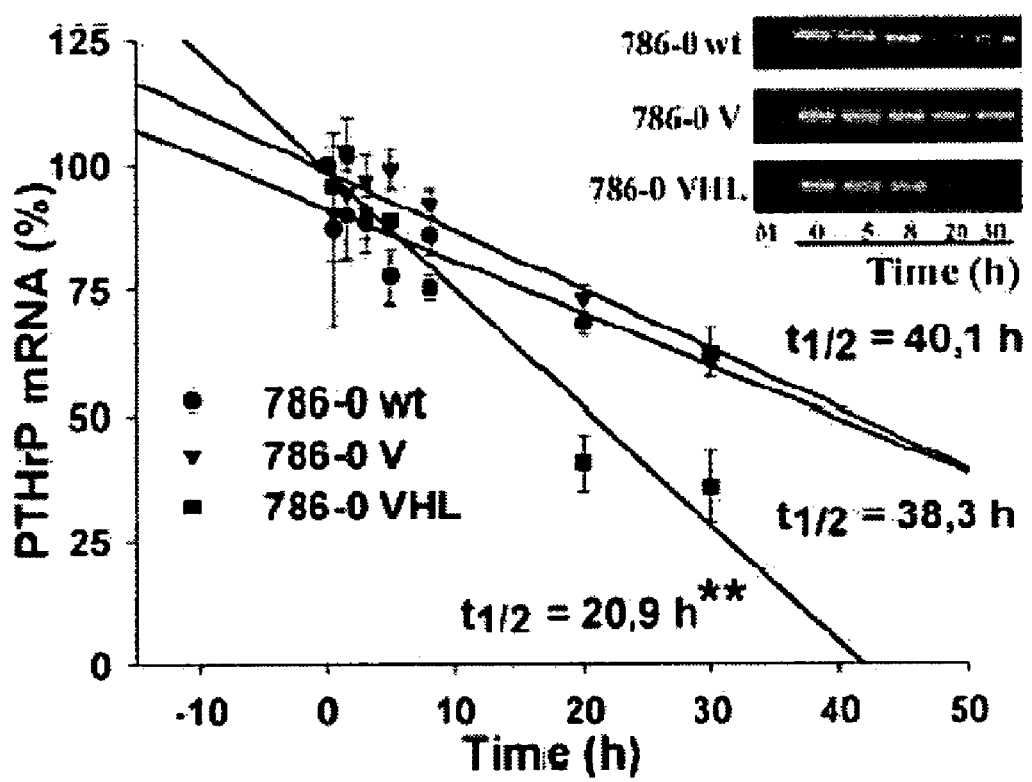

FIG. 19: Decrease of the mRNA transcript of hPTHrP in the non-transfected 786-0 cells, the clones 3 and 4 of 786-0 cells transfected by the vector, the clones 2 and 3 of 786-0 cells transfected by the vector encoding VHL.

Other aspects and advantages of the present invention will appear during the reading of the following examples which must be considered as illustrative and not limitative.

EXAMPLES

Unless stated to the contrary, the percentages given are expressed in weight. Yld means yield.

Materials.

The RPTH1 antagonist, (Asn10, Leu11, D-Trp12)PTHrP (7-34) amide (human, rat) and the anti-PTHrP(1-34) antibody (human, rat) were obtained from Bachem (Bachem Biochimie Sarl, Voisins-le-Bretonneux, France). The anti-PTHrP (34-53) antibody (Ab-2, human) was obtained from Oncogene (France Biochem, Meudon, France) and the anti-PTHrP (107-139) antibody (human) was a gift of Dr P. Esbrit (Fundacion Jimenez Diaz, Madrid, Spain).

Cells Lines and Culture.

The human tumour cell line 786-0 was obtained from ATCC (American Type Culture Collection, Manassas, Va., USA), for which the distributor in Europe is LGC Promochem (Teddington, UK). The human tumour cell lines UOK-126 and UOK-128 were supplied by Dr P. Anglard, (IGBMC, Strasbourg, France). The cell line 786-0 (ATCC CRL-1932) corresponds to cells from a metastatic human CCC (lungs) mutated for the VHL gene [loss of 1 allele and partial deletion of the second one producing a VHL of 104 amino acids, VHL (1-104), instead of VHL(1-213)] and being tumorigenic (Williams et al, In Vitro, 12: 623-627, 1976), the cell line UOK-126 corresponds to cells from a human CCC, loss of heterozygotia on the chromosome 3p (Anglard et al, Cancer Res., 52: 348-356, 1992) and the cell line UOK-128 corresponds to cells from a human CCC, loss of heterozygotia on the chromosome 3p (Anglard et al, Cancer Res., 52: 348-356, 1992).

The 786-0 cells were maintained in culture in a RPMI 1640 medium (Invitrogen Sarl, Cergy Pontoise, France) containing 300 mg/l of L-Glutamine and supplemented with $NaHCO_3$ (20 mM), D-Glucose (25 mM), HEPES buffer (10 mM), sodium pyruvate (1 mM), bovine foetal serum (10%; Invitrogen Sarl) and a mixture of antibiotics (penicillin 100 U/ml and streptomycin 100 µg/ml) at 37° C. in an environment containing 10% of $CO_2$ in the air. The UOK-126 and UOK-128 cells were maintained in culture in a DMEM (Dulbecco Modified Eagle Medium) medium containing 10% bovine foetal serum and the mixture of antibiotics at 37° C. in an environment containing 10% $CO_2$ in the air. For the proliferation assays, the cells were sub-cultivated (passage) by digestion with trypsin (Sigma, St. Quentin Fallavier, France) and treated according to the conditions described below.

Animals.

Athymic male mice, nude, Swiss Nu/Nu, aged 7 weeks on their arrival and weighing approximately 30 g were obtained from Iffa-Credo (L'Arbresle, France). The mice were accommodated in protected and ventilated enclosures in conditions free of pathogens under a diurnal cycle 12 hrs—nocturnal 12 hrs and with free access to food and to drinking water previously autoclaved.

Isolation of the RNA and Analysis of the Expression by RT-PCR.

The total RNA is extracted from tumour cells in culture by the Trizol technique (Invitrogen Sarl) according to the protocol defined by the supplier. Total cDNA is obtained by reverse transcription (RT) on 2.5 at 10 µg total RNA in a mixture containing 200 U of reverse transcriptase (Fermentas—Euromedex, Souffelweyerheim, France), 10 U RNase inhibitor (Invitrogen Sarl), 1 mM triphosphate deoxynucleotides (dNTP, Invitrogen Sarl) and 1 µM non-specific compound $p(dT)_{15}$ (Roche Diagnostics, Meylan, France) for 1 hr at 37° C. The amplification by PCR is performed with 0.15 µM of specific primers:

. either human PTHrP

```
SEQ ID N° 1 (forward): ATG CGA CGG AGA CTG GTT
GAG;

SEQ ID N° 2 (reverse): TCA ATG CCT CCG TGA ATC
GAG CTC CAG CGA CGT (obtained fragment of 535 bp)
or human RPTH1

SEQ ID N° 3 (forward): AGG AAC AGA TCT TCC TGC
TGC A;

SEQ ID N° 4 (reverse): CAC AGC TAC GGT GAG GGA
CGC GAG, (obtained fragment of 515 bp)
or human VHL (Fukuzumi et al, Cancer Letters,
161 :133-140, 2000)

SEQ ID N° 5 (forward): GCG TCG TGC TGC CCG
TAT G;

SEQ ID N° 6 (reverse): TTC TGC ACA TTT GGG
TGG TCT TC (obtained fragment of 340bp),
or human GAPDH SEQ ID N° 7 (forward): GGA AGG TGA AGG TCG
GAG TC.

SEQ ID N° 8 (reverse): GCA GTG ATG GCA TGG
ACT G.
```

0.4 mM dNTP, 2.5 U REDTAQ DNA polymerase (Sigma) and 0.5 µg (PTHrP) or 1 µg (RPTH1) cDNA. PCR begins with denaturation at 95° C. for 4 min, then the cycles are programmed in the following way: 1 min at 94° C. (denaturation), 1 min at 60° C. (annealing) and 1 min at 72° C. (synthesis). PCR is launched for 30 cycles for PTHrP and RPTH1. The last cycle is followed by an additional extension of 8 min at 72° C. The PCR products are separated by electrophoresis on agarose gel at 2% in the presence of 0.5 µg/ml ethidium bromide. The intensity of the bands obtained after electrophoresis is quantified by gel analysis software (SigmaScanPro 4.01, Jandel Scientific, Erkrath, Germany).

Radioimmunological Dosage (RIA) of PTHrP

The tumour cells were cultivated until confluence under normal culture conditions (medium containing 10% serum as described above). The conditioned culture medium of the cells were thus recovered and freezed immediately at −80° C. In certain assays, the cells were cultivated up to 80% confluence, then the culture medium was changed for a fresh medium. The cells were thus left for a further 24 hrs, then the medium was recovered (dosage of the PTHrP secretion in 24 hrs). The PTHrP is then dosed by a radioimmunological method using an antibody specifically recognising the amino-terminal part of PTHrP (kit RIA, Bachem).

Western Blot

The expression of the proteins was analysed as described in Massfelder et al (2002, *J. Am. Soc. Nephrol.* 13, 639-648) over 10-30 µg proteins using a mouse monoclonal antibody anti-HA (Roche Diagnostics, Myelan, France) in order to detect pVHL or an anti-hRPTH1 antibody. A mouse polyclonal antibody anti-β, actin (Sigma-Aldrich) was used to visualise the protein charge of the gel.

Immunofluorescence of PTHrP and RPTH1.

The cells were prepared as described in Massfelder et al (1997, *Proc. Natl. Acad. Sci. USA* 94, 13630-13635). Polyclonal rabbit antibodies purified by affinity directed against either PTHrP(1-34) (N-term Ab) (Bachem) or hRPTH1 (Eurogentec, Angers, France) were used at 5 µg/ml. An anti-rabbit secondary antibody conjugated with TRITC was used for the detection. As a control, a non-immunised rabbit IgG (Sigma-Aldrich, St Quentin Fallavier, France) was used instead of the primary antibody.

Plasmids and Stable Transfection.

Expression vector. The plasmid pCR3.1-Uni was used, in which the full-length cDNA of human VHL (encoding a protein of 213 amino acids) was sub-cloned. In the control transfections, we used the pCR3.1-Uni vector alone.

Transfection protocol. The 786-0 cells were cultured in 75 cm$^2$ culture vessels in the RPMI 1640 medium (cf above) supplemented by 10% serum up to 50% confluence. The adherent cells were then washed 3 times with 10 ml of medium without serum and then maintained in 5 ml of this same medium. In order to transfect the cells, 5 µg of plasmidic DNA (pCR3.1-Uni alone or pCR3.1-Uni VHL) in 50 µl water were incubated with 50 µl LIPOFECTAMIN (Invitrogen Sarl) at 2 mg/ml for 30 mins at room temperature. This solution is added drop by drop to the cells, then the containers are incubated for 4 hrs at 37° C. After this incubation period, 10 ml of RPMI 1640 medium supplemented by 10% serum were added to the cells. After 24 hrs, the medium is replaced by fresh medium containing 10% serum. Two days later, the medium is replaced by a medium supplemented by 10% FBS and containing 500 µg/ml G418 (neomycin) in order to select the transfected cells. The optimum concentration of G418 was determined for the 786-0 cells by a "death curve" over 3 weeks with concentrations of 25 to 1000 µg/ml of G418 and change of medium every 3 days. For each transfection (vector alone or pCR3.1-Uni VHL), 3 clones were selected as well as all clones (all the clones brought together) and maintained in the RPMI 1640 medium with serum and supplemented by 500 µg/ml G418.

Measurement of Cell Proliferation.

Treatments of the Cells.

The cells were cultured in plates with 24 wells (1 ml per well) and in plates with 96 well (100 µl per well) at the rate of 10,000 to 30,000 C/ml. The cells were cultivated in the medium with serum described above. For the assays with the RPTH1 antagonists, after 24 hrs of culture, the medium was changed for a medium without serum containing 0.1% BSA (bovine serum albumin, Sigma) and the antibiotics. This manipulation facilitates cultivation of the cells in the absence of the factors present in the serum and facilitates assessment of the influence of the antagonist on cell proliferation. After 24 hrs, the culture medium are replaced by a medium which is still without serum but containing either the antagonist (Asn10, Leu 11, D-Trp12)PTHrP(7-34) amide at different concentrations, or the diluent (control), for 48 hrs. For the assays with the anti-PTHrP antibodies, the culture medium with serum is maintained and, after 24 hrs of culture, the cells are cultivated in the presence of PTHrP (anti-PTHrP(1-34) antibodies at 1.5 µg/ml, anti-PTHrP(34-53) at 2 µg/ml, anti-PTHrP(107-139) at 5 µg/ml or purified IgG (5 µg/ml, Sigma) for a further 48 hrs.

The cell proliferation was determined by two means, on the one hand by counting the cells (manual counting) using plates with 24 wells and on the other hand by measuring the incorporation of 5-bromo-2'-deoxyuridine (BrdU) using plates with 96 wells.

Counting of the Cells.

The culture medium is removed by suction and an adequate volume of trypsin-EDTA (Sigma) is added. The plates with 24 wells are thus placed into the incubator at 37° C. for 5 to 10 min until the cells are well detached from the bottom of the plates and in individual suspension, which is followed under optic microscope. The cells are then recovered and manually counted with a counting cell placed under an optic microscope. One well is used per experimental condition.

Measurement of the Incorporation of BrdU

The principle of the used test is as follows: the BrdU, an analogue of the pyrimidines, is incorporated in place of the thymine in DNA of the cells in proliferation. The measurement of the incorporation of BrdU is an index of the DNA synthesis. The test is performed with a calorimetric reaction kit commercially available (Roche Diagnostics) and according to the protocol described by the supplier. The developed colour, and thereby the absorbency values observed at a visible wavelength, are directly correlated with the rate of DNA synthesis and thus with the number of cells in proliferation in the different cultures.

Analysis of the Cell Death/Apoptosis

The cells were treated under control conditions or with either an anti-PTHrP N-terminal antibody at 1.5 µg/ml or a RPTH1 antagonist at 1 µM for 48 hrs. The orange acridine (OA) and the ethidium bromide (EB) were dissolved in a PBS buffer and added at 2 µg/ml in the culture medium. The cells were observed and photographed under fluorescence microscopy, either for the FITC (OA) or for the TRITC (EB). The fragmentation of the internucleosomal DNA was detected by a "DNA laddering" test. The cells were re-suspended in 300 µl of lysis buffer (25 mM EDTA, 1% SDS, 1 mg/ml proteinase K, pH 8) and incubated overnight at 50° C. DNA was extracted by phenol/chloroform, precipitated with ethanol and analysed by electrophoresis on agarose gel.

Measurement of the Activity of the PTHrP Promoter.

The non-transfected 786-0 cells and the clones transfected by the vector or the VHL-vector were transiently transfected with a construct containing the promoter regions (P1, P2, and P3 promoters) of the PTHrP gene linked to a bacterial chloramphenicol acetyltransferase gene (CAT) without any promoter. The transfection was performed 24 hrs after sub-culturing of the cells with 1 µg/cm$^2$ of promoter plasmid PTHrP-CAT or a CAT plasmid without any promoter in the presence of Lipofectamin. The cells were analysed 48 hrs after the transfection for the expression of CAT using the ELISA kit for the CAT enzyme (Roche Diagnostic). The results were standardised and expressed in pg CAT enzyme/ mg of protein.

Actonomycin D Assays

The non-transfected 786-0 cells and the clones transfected by the vector or the VHL vector were exposed to 5 µg/ml actinomycin D (Sigma) for 0-30 h. The total RNA were isolated and the expression of hPTHrP was analysed by RT-PCR using hGAPDH in order to standardise the PCR reactions.

Experimental Protocoles in the Nude Mouse.

Subcutaneous implantation of the 786-0 cells. The 786-0 cells have the particular factor of being tumorigenic in vivo in a nude mouse and are therefore currently used to study the effect of drugs on human tumour growth with this model.

The 786-0 cells were cultivated in the RPMI 1640 medium supplemented with serum until confluence. The cells were recuperated by trypsination and re-suspended in RPMI 1640 medium without serum and without antibiotics at the rate of 5 million cells/200 µl the same day of implantation of the mice. The cells were implanted subcutaneously in the backs of nude mice at the rate of 200 µl per implantation. A week to 10 days after the implantation of the cells, the tumours developed forming nodules of approximately 60 to 300 mm$^3$. From this moment, the treatments were initiated according to three protocols: a pilot protocol which was performed in order to determine the effectiveness of the treatments in vivo and carried out on two mice per experimental condition receiving 4 implantations (namely 8 tumours/experimental condition) and two experimental protocols elaborated following the results obtained with the pilot protocol on 10 or 5 mice per experimental condition and receiving 1 or 2 implantations (namely 10 tumours/experimental condition).

Pilot Protocol. In this protocol, 6 mice were separated into three groups: a first group receiving injections of sterile water (control), a second group receiving injections of anti-PTHrP (1-34) antibody (Bachem, dissolved in sterile water) and a third group receiving injections of antagonist (Asn10, Leu11, D-Trp12)PTHrP(7-34) amide (Bachem, dissolved in sterile water). All injections were performed 2 times per week intra-peritoneally (50 µg/mouse of antibody or 20 µg/mouse of antagonist in 200 µl) and in intra-tumoural terms (25 µg/mouse of antibody or 10 µg/mouse of antagonist in 1001 µl). The control mice received an injection of 200 µl of water intraperitoneally and of 100 µl of water intratumourally. The volume of the tumours (length×width×depth×0.5236) was manually measured in a blind manner with callipers on days 0, 4, 7, 12, 14, 18, 23 and 25 after the first injection of the compounds under light gas anaesthesia with isoflurane. For the "antibody" series, the injections were stopped after 18 days.

First Experimental Protocol. The results of the pilot series showed that the anti-PTHrP antibodies and the RPTH1 antagonist have an effectiveness being equal in respect of inhibiting the tumoural growth of the tumours implanted in the nude mouse. Consequently, in this protocol, on the one hand the numbers in each group were increased (10 mice with a tumour/experimental group) and on the other hand daily injections either of water (control) or of the RPTH1 antagonist (dissolved in sterile water) were performed. As for the pilot protocol, all the injections were performed intraperitoneally (200 µl water or 20 µg/mouse of antagonist in 200 µl) and intratumourally (100 µl of water or 10 µg/mouse of antagonist in 100 µl). For this series, the size of the tumours was measured in a blind way twice a week under light gas anaesthesia with isoflurane. At the end of the experimental period, the mice were anaesthetised with pentobarbital. Approximately 0.5 ml of blood was then recovered rapidly through intracardiac puncture of each mouse for the dosage of electrolytes and circulating PTHrP. The tumours were dissected and fixed in formol for subsequent histo-pathological studies (necrotic aspect) and immunohistochemical studies (factor VIII, PTHrP, RPTH1, mitotic index and apoptotic index).

Second Experimental Protocol. In parallel, an experimental protocol was also performed for the anti-PTHrP (N-term) antibodies with daily intraperitoneally injections with 40 µg/mouse either of anti-PTHrP (N-term) antibody or of non-specific IgG (5 mice with 2 tumours/experimental group).

Proliferative and Apoptotic Index. The proliferation index was determined by coloration of tumour section with a monoclonal mouse antibody anti-Ki67 human, Dako, Trappes, France) using standard methods. The detection kit of apoptotic cells based upon the TUNEL method (Roche Diagnostics) was used to measure the apoptotic index on the sections. The total cells and those coloured in 15 fields (0.25 mm$^2$ each) of the highest cell coloration were counted in order to determine the two indexes which are expressed as a percentage of coloured cells in relation to total cells.

Factor VIII and Microvascular Density. The tumour sections were coloured for the endothelial cells with a rabbit polyclonal antibody anti-human factor VII, (Dako) using standard methods. The density of the micro-vessels was determined by counting the intersection points between vessels and the total number of vessels of 4 to 5 fields (0.25 mm$^2$ each) showing the highest vascular density.

Statistics

For the experiments in vitro, the results of the manual counts are expressed as a percentage of the number of cells present in the control wells. In order to calculate the incorporations of BrdU in response to the treatments, all the obtained OD values are decreased by the mean of the OD obtained for the negative control wells. The incorporations in response to the treatments are thus expressed as a percentage of the incorporations of positive controls taken as 100% incorporation. The results are expressed as a mean +/−ESM and were compared by test-t or test-t paired. A value of P at least <0.05 is considered as reflecting a significant difference.

For the experiments in vivo in the nude mouse, the results of tumour growths were expressed as a percentage of the size at day 0 of the treatments. The results are expressed as a mean +/−ESM. The growth of the tumours according to the treatments was compared by test-t in order to evaluate the differences between the treatments and by test-t paired in order to assess the development of the tumour growth in each experimental condition. A value of P at least <0.05 is considered as reflecting a significant difference.

Results

The gels showing the expression of PTHrP and RPTH1 at the level of mRNA in 3 samples (numbered 1, 2 and 3) of the 3 tumour lines 786-0, UOK-126 and UOK-128 are given in FIG. 2. Experiments performed by RT-PCR.

It is thus easy to ascertain that the three lines express PTHrP and RPTH1.

The results represented in FIG. 3 show that the 3 tumour cell lines express PTHrP on the protein level.

In comparison, the secretion of immuno-reactive PTHrP is not detectable in the vascular smooth muscular cells for example while the expression of PTHrP can be observed by RT-PCR (data not shown).

With the results obtained by RT-PCR, it is concluded that the 3 cell lines express PTHrP at the level of the messenger and at the level of the protein which facilitates the envisaging of the autocrine/paracrine effects of the PTHrP on the proliferation of the cells.

In cells in culture, PTHrP and RPTH1 were localised by immunofluorescence in the cytosol and in the nucleoles. The labelled pattern was identical for the three cell types.

FIG. 4 represents the effect of the antibodies directed against the different regions of the PTHrP on the proliferation of the tumour cells 786-0 in vitro measured by the number of cells (on the left) and by the incorporation of BrdU (on the right). FIG. 4 shows that the different antibodies inhibit by 20% to 60% the cell proliferation suggesting an auto/paracrine effect of the secreted PTHrP on the proliferation of the cells.

The fact that the three antibodies inhibit the proliferation of these cells suggests that these cells secrete amongst other things large amino-terminal fragments recognised by the three antibodies.

N-term: anti-PTHrP(1-34) antibody (Bachem) 1.5 μg/ml
Int. region: anti-PTHrP (34-53) antibody (Ab-2, Oncogene) 2 μg/ml
C-term: anti-PTHrP(107-139) antibody (P. Esbrit, Madrid, Espagne) 5 μg/ml
IgG: (Sigma) 5 μg/ml
Number of independent experiments: n=8-12 (FIG. 4 on the left); n=4 (FIG. 4 on the right).

FIG. 5 shows the effect of the RPTH1 antagonist, (Asn10, Leu11, D-Trp12)hPTHrP(7-34) amide at different concentrations on the proliferation of the tumour cells 786-0 in vitro measured by the number of cells (on the left) and by the incorporation of BrdU (on the right). These results clearly show the capacity of the antagonist to inhibit very strongly at 70% the cell proliferation.

Number of independent experiments: n=12 (FIG. 5 on the left); n=7-15 (FIG. 5 on the right).

FIG. 6 represents the effect of the antibodies directed against the different regions of PTHrP on the proliferation of the UOK-126 tumour cells in vitro measured by the number of cells (on the left) and by the incorporation of BrdU (on the right). The figure shows that the different antibodies inhibit from 20% to 30% the cell proliferation suggesting an auto/paracrine effect of the secreted PTHrP on the proliferation of the cells. Only the antibody directed against the C-term part does not show effectiveness. This can be explained by either a too strong dilution of the antibody or by the fact that these cells secrete amino-terminal fragments of PTHrP but do not present C-terminal immunoreactivity. Number of independent experiments: n=4-12 (FIG. 6 on the left); n=4-12 (FIG. 6 on the right).

FIG. 7 shows the effect of the RPTH1 antagonist, (Asn10, Leu11, D-p12)hPTHrP(7-34) amide at different concentrations on the proliferation of tumour cells UOK-126 in vitro measured by the number of cells (on the left) and by the incorporation of BrdU (on the right). These results clearly show the capacity of the antagonist to also inhibit very strongly the cell proliferation.

Number of independent experiments: n=8 (FIG. 7 on the left); n=8 (Figure on the right).

FIG. 8 shows the effect of the antibodies directed against the different regions of PTHrP on the proliferation of the tumour cells UOK-128 in vitro measured by the number of cells (on the left) and by the incorporation of BrdU (on the right). The figure shows that the different antibodies inhibit by 20% to 40% the cell proliferation suggesting an auto/paracrine effect of secreted PTHrP on the proliferation of the cells. Similarly to the UOK-126 cells, only the antibody directed against the C-term part shows a limited effectiveness. With the results obtained on the UOK-126 line, these results suggest that this weakness in effectiveness is due to a too strong dilution of the antibody. However, this antibody was not in sufficient amount to increase the concentration of the antibody in the medium. Number of independent experiments: n=4-12 (FIG. 8 on the left); n=4-12 (FIG. 8 on the right).

FIG. 9 shows the effect of the RPTH1 antagonist, (Asn10, Leu11, D-Trp12)hPTHrP(7-34) amide at different concentrations on the proliferation of the tumour cells UOK-128 in vitro measured by the number of cells (on the left) and by the incorporation of BrdU (on the right). Similarly, these results clearly show the capacity of the antagonist to strongly inhibit the cell proliferation.

Number of independent experiments: n=8 (figure on the left); n=8 (figure on the right)

In FIGS. 4 to 9:
* signifies $p<0.05$ in comparison to the control
** signifies $p<0.01$ in comparison to the control FIG. 10 shows the reproduction of photographs of the 786-0 cells in culture in a RPMI 1640 medium without serum (with 0.1% BSA) and treated either as a control (on the left) or in the presence of $10^{-6}$ M of the antagonist (Asn10, Leu11, D-Trp12)hPTHrP(7-34) amide (on the right) for 48 hrs.

It is clearly observed that the antagonist has the effect of detaching the cells from the culture support causing them to completely lose their adherence.

This effect can be due to a toxic effect and/or an apoptotic effect and/or a necrotic effect and/or an anoikitic effect (cell apoptosis by detachment of the cells).

Figure 11B:
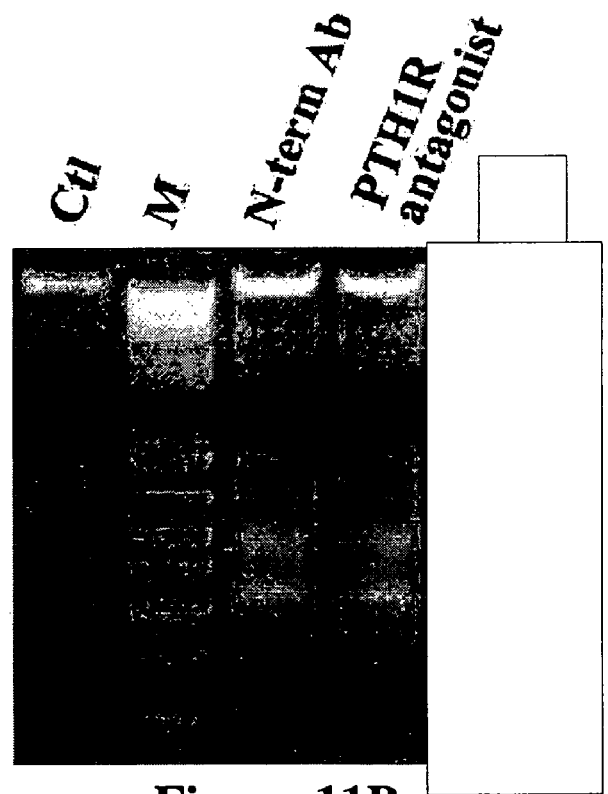

FIG. 11 shows the effect of the RPTH1 antagonist, (Asn10, Leu11, D-Trp12)hPTHrP(7-34) amide and of an antibody directed against the N-terminal end of PTHrP (N-term Ab) on the apoptosis of the tumour cells 786-0. In order to determine whether the inactivation of PTHrpP/RPTH1 induces cell death, the inventors examined simultaneously OA et EB colouration for a control and for the treated CCR cells. EB impregnates the living cells, acting solely as a marker of cell death while OA freely impregnates and visualises all the cells of the field. The exposure to a RPTH1 antagonist clearly increases the number of cells marked by EB compared with the non-treated cells (FIG. 11A). The analysis of the genomic DNA in the treated 786-0 cells revealed a fragmentation of the internucleosomal DNA (scale at 180 pb) which is specific of the cell death by apoptosis (FIG. 11B). The cell detachment, the colouration as well as the fragmentation of the internucleosomal AND were observed for all the cell lines and whatever the means used to block the PTHrP/RPTH1 system. These results suggest strongly that PTHrP acts as an essential growth and survival factor for the CCR cells.

FIG. 12 shows the growth of the tumours of the mice treated either as a control or by the antibody or by the antagonist according to the pilot protocol described above. The growth results are expressed as a percentage in relation to day 0 of the start of the treatments.

It is easy to ascertain that the control tumours grow very significantly while the tumours of the mice treated either by the anti-PTHrP(1-34) antibody or by the antagonist have a considerably slowed-down growth in relation to the growth of the tumours of the mice treated as controls.

The photographs show, above, a mouse treated as a control for 25 days with its 4 easily observable tumours and, below, a mouse treated for 25 days by the antagonist. The effectiveness of the antagonist in inhibiting the tumour growth is clear.

Number of independent experiments: n=8 (4 tumours/mouse, 2 mice/experimental conditions)

* signifies p<0.05 for the growth of the tumours of the mice treated by the antibody or the antagonist in comparison to the growth of the tumours of the mice treated as a control on the same day.
** signifies p<0.01 for the growth of the tumours of the mice treated by the antibody or the antagonist in comparison to the growth of the tumours of the mice treated as a control the same day.
signifies p<0.01 for the growth of the tumours of the mice treated as a control in comparison to the day 0 of treatment (significant growth with effect from day 7)
signifies p<0.01 for the growth of the tumours of the mice treated by the antibody or the antagonist in comparison to day 0 (significant growth with effect from day 12 only)

From statistical studies, it appears that the twice weekly treatment of the mice with the antibody or the antagonist is sufficient to greatly slow down tumour growth in comparison with the control growth but not to completely inhibit this growth. It is for this reason that, in the experimental series, it was decided to inject the antagonist every day in order to evaluate whether the antagonist is capable of completely inhibiting tumour growth, even causing it to regress. In the experimental series, the number n of mice was increased to 10 per experimental condition.

FIG. 13 shows the growth of the tumours of the mice treated either as a control or by the antagonist according to the experimental protocol described above. The growth results are expressed as a percentage in relation to day 0 of the start of the treatments.

It is ascertained once again that the control tumours grow very significantly while the tumours of the mice treated by the antagonist have a growth which is totally inhibited (thus blocked) in comparison to the growth of the tumours of the mice treated as a control. This study reveals that the antagonist exerts at least cyto-static effects on the tumours.

Number of independent experiments: n=10 mice (1 tumour/mouse) per experimental condition

* signifies p<0.05 for the growth of the tumours of the mice treated by the antagonist in comparison to the growth of the tumours of the mice treated as a control the same day
** signifies p<0.01 for the growth of the tumours of the mice treated by the antagonist in comparison to the growth of the tumours of the mice treated as a control the same day
signifies p<0.05 for the growth of the tumours of the mice treated in comparison to day 0 of treatment (significant growth with effect from day 3)
signifies p<0.01 for the growth of the tumours of the mice treated as a control in comparison to day 0 of treatment From statistical studies, it appears this time that the daily treatment of the mice with the antagonist completely blocks the tumour growth. Certain tumours have even regressed.

FIG. 14 shows the growth of the tumours of the mice treated either by an antibody directed against the N-terminal extremity of PTHrP or by non-specific IgG according to the protocol described above. The growth results are expressed in comparison to day 0 of the start of the treatments. Surprisingly and impressively 7 tumours disappeared while the other 3 regressed by 50% to 80% in the mice treated with the antibodies in comparison to the controls.

Number of independent experiments: n=10 tumours (2 tumours/mouse) per experimental condition signifies p<0.01 for the growth of the tumours of the mice treated as a control in comparison to day 0 of treatment
** signifies p<0.01 for the growth of the tumours of the mice treated with the antibody in comparison to the growth of the tumours of the mice treated as a control the same day Since 70% of the tumours disappear with the treatment with an anti-PTHrP antibody and the remaining tumours are too small, the histopathological analysis were performed on the tumours of animals treated with a RPTH1 antagonist and their control. No polymorphic difference was detected between the two groups. The tumours obtained from the control mice strongly express PTHrP and RPTH1 with a clear colouration observed in the cytoplasm of all the cells and in the nucleole of various cells. The proliferation index was not different between the control and treated groups. However, the treatment by the RPTH1 antagonist increased twofold the apoptotic index. In addition, the number of intersection points of the vessels and the total number of vessels per surface area were significantly increased.

Globally, the targeting system PTHrP/RPTH1 is not only effective against CCR through an increase of the apoptosis of the tumour cells but also appears not to have harmful secondary effects In FIG. 15 shown on the left the pCR3.1-Uni vectors, alone or coding for VHL(1-213). These vectors have been transfected in the 786-0 cells (cf above.). Three individual clones were isolated after selection by G418 as well as all of the clones for the transfected cells by the vector alone (786-0 V, individual clones 2, 3, 4 and mixed clones p) or by the coding vector for VHL (786-0 VHL, individual clones 2 3 and 6 and mixed clones p). Parallel to these clones, 3 samples of non-transfected 786-0 cells (786-0 wt for wild-type) and 3 samples of HK-2 cells (normal human proximal tubular cells) were also tested for the expression of VHL and of PTHrP.

The gels show the expression of VHL obtained by RT-PCR on the total RNA isolated from the different cells (band at 340 bp) according to the protocol described above. It is easy to ascertain that the normal HK-2 cells express 2 times more VHL than the 786-0 wt cells (1 allele of the absent VHL gene). In the clones transfected with the vector alone the expression of VHL is equivalent to that which is found in the non-transfected 786-0 cells. On the other hand in the clones transfected by the VHL, the expression of VHL is very much increased which shows that the transfection is very effective. If we now consider the expression of PTHrP in the different clones and cell types, it is easy to observe an inverse correlation between the expression of VHL and the expression of PTHrP. These results show that the PTHrP at the level of its messenger is a direct or indirect target of the tumour suppressing gene VHL. In order to confirm this at the level of the protein itself (immunoreactive PTHrP), the conditioned medium of 786-0 wt, V and VHL were recovered. The results are represented in FIG. 17. In addition, the Western Blots of FIG. 16 allow estimation of the levels of protein for VHL.

FIG. 17 on the left shows through RIA of PTHrP, in conditioned medium of cells at confluence, that the production of PTHrP is reduced by 50% in the transfected 786-0 cells with the plasmid encoding VHL (786-0 VHL) in comparison with the non-transfected cells (786-0 wt) or those transfected with the vector alone (786-0 V).

In order to confirm this result, the cells were cultivated up to 80% confluence, then the medium changed for fresh medium and left 24 hours in order to measure the PTHrP secretion in 24 hrs. The cells were counted in parallel in order to express the PTHrP secretion per 24 hrs and per million cells. The results of these experiments are shown in FIG. 17 on the right representing the PTHrP secretion in pM per 24 hrs and per million cells. There again, it is easily ascertained that the PTHrP secretion is reduced by 50% in the 786-0 VHL cells in comparison to the non-transfected control cells or those transfected by the vector alone. In addition, the expression of RPTH1 is not affected by pVHL. Thus, PTHrP is repressed by pVHL. These results show, with those presented in FIG. 15, that PTHrP is a direct or indirect target (for example via HIF—hypoxic-induced factor) of the product of the VHL gene in the tumour cells.

Number of independent experiments: n=12-14 (figure on the left) and n=5 (figure on the right)

* Signifies p<0.01 for the secretion of PTHrP of the cells 786-0 VHL in comparison to the control cells 786-0 wt and 786-0 V In order to analyse whether PHrP is regulated by pVHL at the transcriptional level, the inventors transciently transfected the non-transfected 786-0 cells, the clones 3 and 4 of 786-0 cells transfected by the vector alone, the clones 2 and 3 of 786-0 cells transfected by the vector encoding VHL with a CAT expression vector containing the promoter regions of the human PTHrP gene and they measured the CAT enzyme in the cell extracts. The reintroduction of the VHL gene in the 786-0 cells does not alter the transcriptional activity of the PTHrP promoters (FIG. 18) suggesting that the regulation is post-transcriptional. The analysis of the stability of the PTHrP mRNA in the non-transfected 786-0 cells, the clones 3 and 4 of 786-0 cells transfected by the vector alone, the clones 2 and 3 of 786-0 cells transfected by the vector encoding VHL subjected to a transcriptional inhibitor, actinomycin D, shows in fact that the half-life of the PTHrP mRNA was 38.3±3 hrs and 40.1±3.4 hrs for the non-transfected 786-0 cells and the 786-0 cells transfected by the vector alone, respectively, and reduced by 50% to 20.9±2.6 h for the 786-0 cells transfected by the vector encoding VHL (FIG. 19). Thus, pVHL decreases the expression of PTHrP in CCR by destabilising the PTHrP mRNA.

This link between PTHrP and VHL strongly suggests that PTHrP can be involved in the growth of the majority of CCC and consequently that the use of the anti-PTHrP antibodies or the RPTH1 antagonists constitutes a therapeutic tool in humans which is very promising for fighting against this disease. All the results presented here in vitro et in vivo push widely in this sense.

The invention claimed is:

1. A method for treating a kidney cancer comprising the administration to a subject of an effective dose of a PTHrP antagonist for inhibiting or decreasing a tumor growth or a pharmaceutical composition containing it, said PTHrP antagonist being an anti-PTHrP antibody that binds amino acids 34-53 of PTHrP.

2. Method according to claim 1, wherein said subject is a human subject.

3. Method according to claim 1, wherein said kidney cancer is selected from the group consisting of papillary carcinoma (chromophiles), chromophobe cell carcinoma, Bellini carcinoma and unclassified renal cell carcinomas.

4. Method according to claim 3, wherein said kidney cancer is clear cell carcinoma (CCC).

5. Method according to claim 1, wherein the kidney cancer is a solid malignant tumour.

6. Method according to claim 1, wherein the PTHrP antagonist is a compound binding the PTHrP receptor and inhibiting partially or totally a binding of PTHrP to its receptor.

7. Method according to claim 6, wherein the PTHrP antagonist is a PTHrP receptor antagonist.

8. Method according to claim 7, wherein the PTHrP antagonist is a PTHrP competitive antagonist.

9. Method according to claim 1, wherein the PTHrP antagonist is a compound binding a ligand of the PTHrP receptor, and inhibiting partially or totally a binding of PTHrP to its receptor.

10. Method according to claim 1, wherein the PTHrP antagonist is a humanised anti-PTHrP antibody.

11. Method according to claim 1, wherein the anti-PTHrP antibody is selected from a humanised antibody, a human antibody, a chimeric antibody, an antibody obtained from a hybridoma and a fragment thereof and a modified form of said fragment.

12. Method according to claim 1, wherein the anti-PTHrP antibody is a polyclonal or monoclonal antibody.

* * * * *